US 12,289,825 B2

(12) United States Patent
Ueda

(10) Patent No.: US 12,289,825 B2
(45) Date of Patent: Apr. 29, 2025

(54) DEVICE COMPRISING STACKED CIRCUIT MEMBERS

(71) Applicant: JAPAN AVIATION ELECTRONICS INDUSTRY, LIMITED, Tokyo (JP)

(72) Inventor: Shinji Ueda, Tokyo (JP)

(73) Assignee: JAPAN AVIATION ELECTRONICS INDUSTRY, LIMITED, Tokyo (JP)

( * ) Notice: Subject to any disclaimer, the term of this patent is extended or adjusted under 35 U.S.C. 154(b) by 136 days.

(21) Appl. No.: 18/102,826

(22) Filed: Jan. 30, 2023

(65) Prior Publication Data

US 2023/0247761 A1 Aug. 3, 2023

(30) Foreign Application Priority Data

Feb. 3, 2022 (JP) ................................. 2022-015704

(51) Int. Cl.
*H05K 1/02* (2006.01)
*H01L 23/10* (2006.01)
(Continued)

(52) U.S. Cl.
CPC .......... *H05K 1/0277* (2013.01); *H01L 23/10* (2013.01); *H01L 23/49838* (2013.01);
(Continued)

(58) Field of Classification Search
CPC .............. H05K 1/0277; H05K 1/0298; H05K 2201/05; H05K 1/111; H05K 3/281;
(Continued)

(56) References Cited

U.S. PATENT DOCUMENTS 3,409,732 A * 11/1968 Dahlgren ............... H05K 1/118
174/254
4,015,328 A 4/1977 McDonough
(Continued)

FOREIGN PATENT DOCUMENTS

| JP | H10189813 A | 7/1998 |
| JP | 2005045111 A | 2/2005 |
| JP | 2021153164 A | 9/2021 |
| WO | 2020170210 A1 | 8/2020 |

OTHER PUBLICATIONS

Extended European Search Report (EESR) dated Jul. 31, 2023, issued in counterpart European Application No. 23154044.4.
(Continued)

*Primary Examiner* — Steven T Sawyer
(74) *Attorney, Agent, or Firm* — Holtz, Holtz & Volek PC

(57) ABSTRACT

A device comprises a first circuit member, a second circuit member and a third circuit member. The first circuit member comprises a first body for performing the function of the first circuit member and a first flexible board formed with a first integrated-electrode portion including first electrodes. The second circuit member comprises a second body for performing the function of the second circuit member and a second flexible board formed with a second integrated-electrode portion including second electrodes. The third circuit member comprises a third body for performing the function of the third circuit member and a third flexible board formed with a third integrated-electrode portion including third electrodes. The first integrated-electrode portion, the second integrated-electrode portion and the third integrated-electrode portion lie over each other in an upper-lower direction. The first body, second body and the third body are apart from each other when seen along the upper-lower direction.

7 Claims, 10 Drawing Sheets

(51) Int. Cl.
*H01L 23/498* (2006.01)
*H05K 1/14* (2006.01)

(52) U.S. Cl.
CPC ........... *H05K 1/0298* (2013.01); *H05K 1/144* (2013.01); *H05K 2201/05* (2013.01); *H05K 2201/052* (2013.01); *H05K 2201/053* (2013.01)

(58) Field of Classification Search
CPC .. H05K 3/4611; H05K 3/4614; H05K 3/4632; H05K 2201/052; H05K 2201/10151; H05K 2203/085; H05K 2203/1147; H05K 3/4691; H05K 1/144; H05K 7/023; H05K 7/026; H01L 23/10; H01L 23/49838; A61B 5/25; A61B 5/259; A61B 2562/164; A61B 2562/166
See application file for complete search history.

(56) References Cited

U.S. PATENT DOCUMENTS

| | | | |
|---|---|---|---|
| 5,266,746 | A | 11/1993 | Nishihara et al. |
| 2015/0005589 | A1 | 1/2015 | Bly et al. |
| 2017/0187156 | A1* | 6/2017 | Wilcock ................. H05K 1/115 |
| 2022/0125408 | A1 | 4/2022 | Ferin et al. |

OTHER PUBLICATIONS

European Office Action dated May 7, 2024, issued in counterpart European Application No. 23154044.4.
European Office Action dated Nov. 15, 2024, issued in counterpart European Application No. 23154044.4.

\* cited by examiner

DEVICE COMPRISING STACKED CIRCUIT MEMBERS

CROSS REFERENCE TO RELATED APPLICATIONS

This application is based on and claims priority under 35 U.S.C. § 119 to Japanese Patent Application No. JP 2022-015704 filed Feb. 3, 2022, the content of which is incorporated herein in its entirety by reference.

BACKGROUND OF THE INVENTION

This invention relates to a device comprising stacked three or more circuit members.

For example, this type of device is disclosed in JP2005-45111A (Patent Document 1), the content of which is incorporated herein by reference.

Referring to FIG. 19, Patent Document 1 discloses a stacked circuit board (device) 90 comprising four circuit boards (circuit members) 92 and three insulation sheets 94. The circuit members 92 are stacked with each of the insulation sheets 94 sandwiched therebetween. Each of the circuit members 92 is formed with a wiring layer 922 made of conductor. Each of the wiring layers 922 is provided with an electrode 926 and various components 924 such as a capacitor. Each of the electrodes 926 is formed with a through-hole 928. The through-holes 928 are located at positions same as each other in the horizontal plane. Each of the through-holes 928 is filled with solder 98. The electrodes 926 are connected to each other by the solder 98, and thereby the wiring layers 922 of the circuit members 92 are electrically connected with each other. The invention of Patent Document 1 provides the device 90 comprising a plurality of the circuit members 92 electrically connected with each other.

Each of the circuit members 92 of Patent Document 1 comprises the various components 924. Accordingly, when the circuit members 92 are stacked to form the device 90, the device 90 tends to have a large height.

SUMMARY OF THE INVENTION

It is therefore an object of the present invention to provide a device which comprises stacked three or more circuit members and can be reduced in height.

An aspect of the present invention provides a device comprising a first circuit member, a second circuit member and at least one third circuit member. The first circuit member comprises a first body and a first flexible board and is formed with a first wiring. The first body and the first flexible board are coupled to each other. The first body has a first main portion configured to perform a function of the first circuit member. The first flexible board has a first integrated-electrode portion. The first integrated-electrode portion is formed with two or more first electrodes. The first wiring connects the first main portion to at least one of the first electrodes. The second circuit member comprises a second body and a second flexible board and is formed with a second wiring. The second body and the second flexible board are coupled to each other. The second body has a second main portion configured to perform a function of the second circuit member. The second flexible board has a second integrated-electrode portion. The second integrated-electrode portion is formed with two or more second electrodes. The second wiring connects the second main portion to at least one of the second electrodes. The third circuit member comprises a third body and a third flexible board and is formed with a third wiring. The third body and the third flexible board are coupled to each other. The third body has a third main portion configured to perform a function of the third circuit member. The third flexible board has a third integrated-electrode portion. The third integrated-electrode portion is formed with two or more third electrodes. The third wiring connects the third main portion to at least one of the third electrodes. The first integrated-electrode portion, the second integrated-electrode portion and the third integrated-electrode portion lie over each other in an upper-lower direction. The third integrated-electrode portion is located between the first integrated-electrode portion and the second integrated-electrode portion in the upper-lower direction. Each of the first electrodes is exposed upward. Each of the second electrodes is exposed downward. Each of the third electrodes has an upper end surface exposed upward and a lower end surface exposed downward, the upper end surface and the lower end surface being electrically connected with each other. At least one of the first electrodes and at least one of the second electrodes are connected to each other via a predetermined one of the third electrodes. The first body, second body and the third body are apart from each other when seen along the upper-lower direction.

According to an aspect of the present invention, the first main portion, the second main portion and the third main portion can be electrically connected with each other via the first integrated-electrode portion, the second integrated-electrode portion and the third integrated-electrode portion which lie over each other. For example, each of the first main portion, the second main portion and the third main portion can be provided with various components such as an integrated circuit (IC) chip and can be provided with a main electrode connectable to an object located outside the device. Thus, the device of an aspect of the present invention can be used as an electronic device comprising three or more electronic circuits connected to each other.

According to an aspect of the present invention, each of the first integrated-electrode portion, the second integrated-electrode portion and the third integrated-electrode portion which lie over each other is formed of a flexible board. The parts which lie over each other can be reduced in height by making each of the flexible boards thinner. Moreover, the first body, the second body and the third body, which are formed with the first main portion, the second main portion and the third main portion, respectively, do not lie over each other in the upper-lower direction. Therefore, even in an instance where each of the first main portion, the second main portion and the third main portion is provided with various components such as an IC chip, the height of the device is not substantially changed as a whole. As can be seen from the explanation described above, an aspect of the present invention provides a device which comprises stacked three or more circuit members and can be reduced in height.

An appreciation of the objectives of the present invention and a more complete understanding of its structure may be had by studying the following description of the preferred embodiment and by referring to the accompanying drawings.

Figure 1:
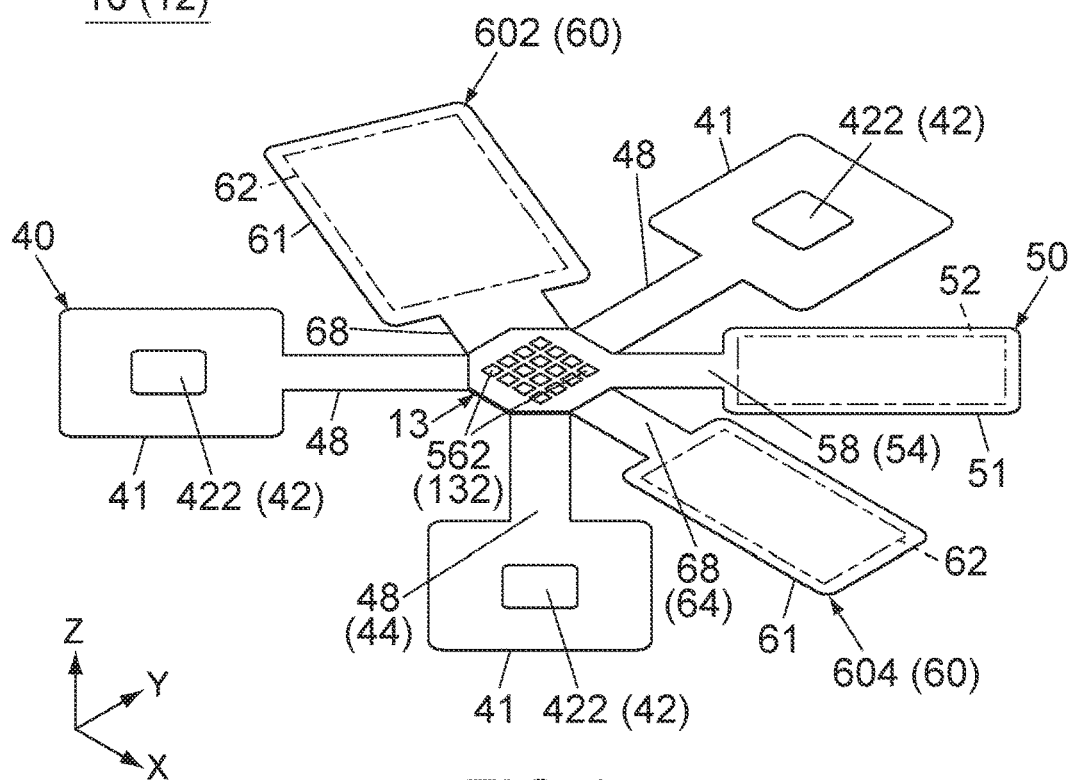
FIG. 1 is a perspective view showing a device according to an embodiment of the present invention, wherein positions of a second main portion and third main portions are illustrated with chain dotted lines.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION

Referring to FIG. 1, a device 10 according to an embodiment of the present invention is an independent electronic device. More specifically, the device 10 can work solely without another electronic device (not shown) physically attached thereto. For example, the device 10 can be attached on a skin near the heart of a subject under a state where the device 10 is accommodated in a sheet-like member as described later. The thus-attached device 10 measures the heart rate and the electric pulse of the heart of the subject and transmits the measurement result to another electronic device. Thus, the device 10 can be used as an electronic device for measuring biological information such as the electric pulse of the heart. However, the present invention is not limited thereto but is applicable to various devices having various functions. For example, the device 10 may be used solely without being accommodated in the aforementioned sheet-like member.

Figure 2:
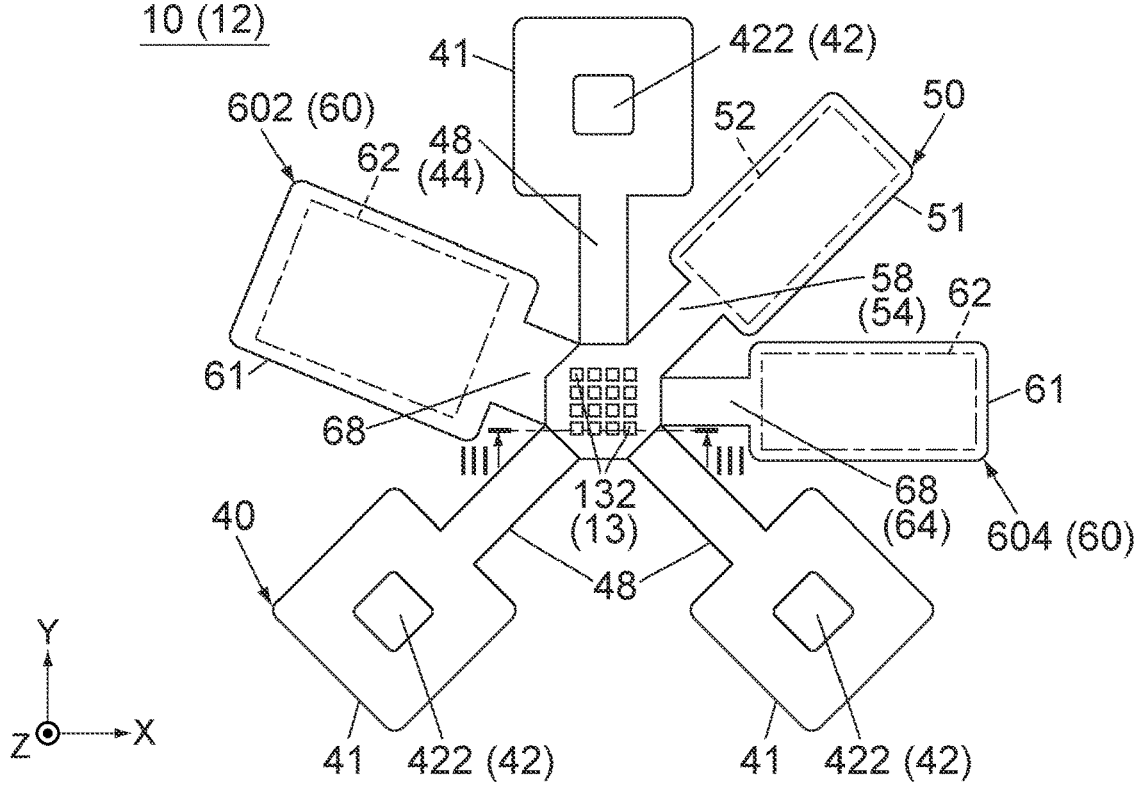
FIG. 2 is a plan view showing the device of FIG. 1, wherein positions of the second main portion and the third main portions are illustrated with chain dotted lines.

As shown in FIGS. 1 and 2, the device 10 of the present embodiment comprises a circuit structure 12. The circuit structure 12 is a member which enables the device 10 to work as an electronic device. The device 10 of the present embodiment comprises only the circuit structure 12. However, the present invention is not limited thereto, but the device 10 may further comprise another member in addition to the circuit structure 12. For example, the device 10 may comprise the aforementioned sheet-like member.

Figure 4:
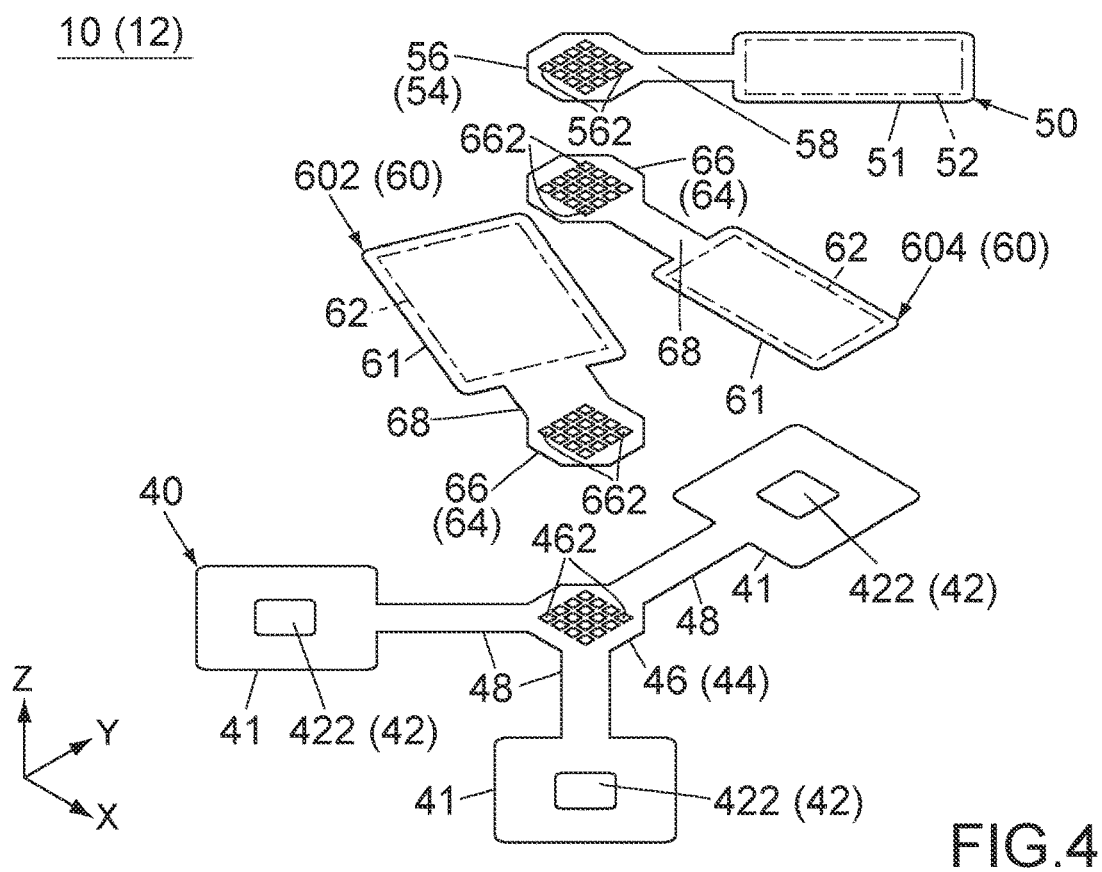
FIG. 4 is an exploded, perspective view showing the device of FIG. 1, wherein positions of the second main portion and the third main portions are illustrated with chain dotted lines.

As shown in FIGS. 1 and 4, the circuit structure 12 of the present embodiment comprises a first circuit member 40, a second circuit member 50 and two third circuit members 60. The third circuit members 60 include a third circuit member 602 and a third circuit member 604. Thus, the device 10 comprises the first circuit member 40, the second circuit member 50, the third circuit member 602 and the third circuit member 604. The second circuit member 50, the third circuit member 604, the third circuit member 602 and the first circuit member 40 are stacked on each other in an upper-lower direction in this order from the top to the bottom and form the single circuit structure 12. The upper-lower direction of the present embodiment is the Z-direction. In the present embodiment, "upward" means the positive Z-direction, and "downward" means the negative Z-direction.

As described above, the circuit structure 12 of the present embodiment comprises four circuit members, or the first circuit member 40, the second circuit member 50 and the two third circuit members 60, which lie over each other. In other words, the function of the circuit structure 12 as an electronic device are divided into four functions which are installed to the four circuit members, respectively. However, the present invention is not limited thereto. For example, the circuit structure 12 may further comprise another circuit member and/or an electronic component in addition to the aforementioned four circuit members. Instead, the circuit structure 12 may comprise only one of the third circuit member 602 and the third circuit member 604. Thus, the device 10 may comprise the first circuit member 40, the second circuit member 50 and at least one of the third circuit members 60.

Hereafter, explanation will be made about each circuit member of the device 10 of the present embodiment.

Figure 5:
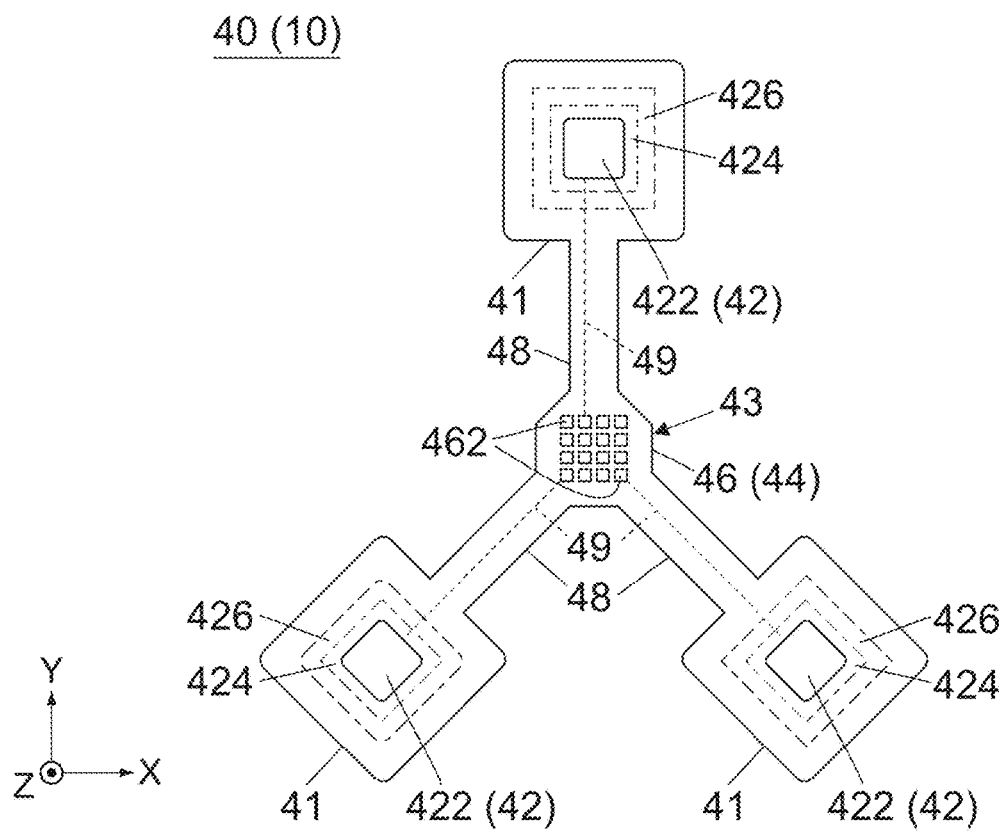
FIG. 5 is a plan view showing a first circuit member of the device of FIG. 4, wherein a hidden first wiring is illustrated with dashed line, and boundaries of exposed portions and boundaries of seal portions are illustrated with chain dotted lines.

Referring to FIGS. 4 and 5, the first circuit member 40 of the present embodiment has a structure described below.

The first circuit member 40 comprises three first bodies 41 and a first flexible board 44. Each of the first bodies 41 is a rigid circuit board which has rigidity and is hardly bent. The first flexible board 44 is a flexible circuit board which is thin and bendable. Each of the first bodies 41 and the first flexible board 44 extends in parallel to a horizontal plane (XY-plane) perpendicular to the upper-lower direction.

The first flexible board 44 and each of the first bodies 41 are coupled to each other in a horizontal direction perpendicular to the upper-lower direction. The first flexible board 44 has a first integrated-electrode portion 46 and three first coupling portions 48 which correspond to the first bodies 41, respectively. Each of the first coupling portions 48 is connected to the first integrated-electrode portion 46 in the horizontal direction. The first coupling portions 48 radially extend from the first integrated-electrode portion 46 in the XY-plane. In other words, the first coupling portions 48 extend from the first integrated-electrode portion 46 in parallel to the XY-plane along various orientations different from each other. Each of the first bodies 41 is connected to the corresponding first coupling portion 48 in the horizontal direction.

The first circuit member 40 of the present embodiment has the aforementioned basic structure. Each of the first bodies 41 is a member different and distinct from the first flexible board 44. Each of the first integrated-electrode portion 46 and the first coupling portions 48 is a part of the single first flexible board 44. However, the present invention is not limited thereto. For example, the number of the first bodies 41 may be one or two or may be four or more. Each of the first bodies 41 may be a part of the flexible circuit board. Each of the first coupling portions 48 may be a rigid circuit board different and distinct from the first flexible board 44. The first coupling portions 48 may be provided as necessary. For example, it is preferable that the first coupling portions 48 each having flexibility are provided when the device 10 is used as a wearable device which fits on a curved surface such as a human body.

The first circuit member 40 of the present embodiment works as a receiver configured to receive electric signals generated by the electric pulse of the heart of a subject (hereafter, referred to "biological signals"). Each of the first bodies 41 has a first main portion 42 configured to perform the aforementioned function of the first circuit member 40. More specifically, each of the first main portions 42 of the present embodiment includes a main electrode 422 made of conductor such as Ag. Each of the main electrodes 422 is a portion for receiving the biological signals from the chest of a subject. Each of the main electrodes 422 is exposed upward.

Each of the first main portions 42 of the present embodiment includes only the one main electrode 422. Thus, the first circuit member 40 of the present embodiment comprises the three main electrodes 422. However, the present invention is not limited thereto. For example, each of the first main portions 42 may include an electronic circuit configured to amplify the biological signals received by the main electrode 422. Thus, each of the first main portions 42 may include various components such as an integrated circuit (IC) chip, a capacitor and an inductor in addition to the main electrode 422. The number of the main electrodes 422 of the first circuit member 40 may be one or two or may be four or more.

The function of the first circuit member 40 of the present invention is not limited to that of the present embodiment. The structure of each of the first main portions 42 can be variously modified in accordance with a function of the first circuit member 40. For example, each of the first main portions 42 may include various components such as an IC chip instead of the main electrode 422.

The first integrated-electrode portion 46 of the present embodiment is a relay portion through which the biological signals received by the main electrodes 422 are transmitted to the third circuit member 604. The first integrated-electrode portion 46 is formed with a first predetermined number of first electrodes 462. The first predetermined number of the present embodiment is sixteen. The first electrodes 462 are arranged in a 4×4 grid. In other words, the first electrodes 462 form a 4×4 grid array. However, the present invention is not limited thereto. For example, the number of the first electrodes 462 may be two. Thus, the first integrated-electrode portion 46 should be formed with two or more of the first electrodes 462.

Each of the first main portions 42 is connected to the first flexible board 44. The first flexible board 44 has a three-layer structure consisting of an upper insulation layer, a wiring layer, and a lower insulation layer, where the upper insulation layer and the lower insulation layer constitute a first insulation layer 43. The wiring layer is located between the upper insulation layer and the lower insulation layer in the upper-lower direction. The wiring layer includes a first wiring 49. Thus, the first circuit member 40 is formed with the first wiring 49.

The first wiring 49 of the present embodiment includes three conductive patterns which correspond to the main electrodes 422, respectively. Each of the conductive patterns of the first wiring 49 connects one of the first electrodes 462 and the corresponding main electrode 422 to each other. The biological signals received by each of the main electrodes 422 are transmitted to the first electrode 462 via the corresponding conductive pattern. The first wiring 49 of the present embodiment has the aforementioned structure. However, the structure of the first wiring 49 of the present invention is not specifically limited, provided that the first wiring 49 connects the first main portions 42 to at least one of the first electrodes 462. The layer structure of the first flexible board 44 of the present invention is not specifically limited.

Figure 7:
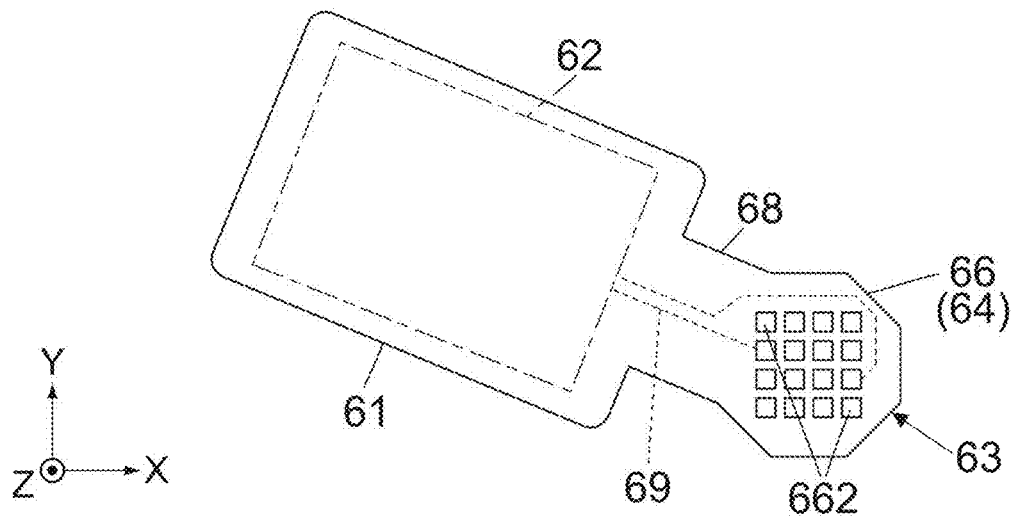
FIG. 7 is a plan view showing one of third circuit members of the device of FIG. 4, wherein a hidden third wiring is illustrated with dashed line, and a position of the third main portion is illustrated with chain dotted lines.

Referring to FIGS. 4 and 7, the third circuit member 602 of the third circuit members 60 of the present embodiment has a structure described below.

The third circuit member 602 comprises a third body 61 and a third flexible board 64. The third body 61 is a rigid circuit board. The third flexible board 64 is a flexible circuit board which is thin and bendable. Each of the third body 61 and the third flexible board 64 extends in parallel to the XY-plane.

The third body 61 and the third flexible board 64 are coupled to each other in a horizontal direction perpendicular to the upper-lower direction. The third flexible board 64 has a third integrated-electrode portion 66 and a third coupling portion 68. The third coupling portion 68 is connected to the third integrated-electrode portion 66 in the horizontal direction and extends from the third integrated-electrode portion 66 along the horizontal direction. The third body 61 is connected to the third coupling portion 68 in the horizontal direction.

The third circuit member 602 of the present embodiment has the aforementioned basic structure. The third body 61 is a member different and distinct from the third flexible board 64. Each of the third integrated-electrode portion 66 and the third coupling portion 68 is a part of the single third flexible board 64. However, the present invention is not limited thereto. For example, the number of the third body 61 may be two or more. The third body 61 may be a part of the flexible circuit board. The third coupling portion 68 may be a rigid circuit board different and distinct from the third flexible board 64. The third coupling portion 68 may be provided as necessary. For example, it is preferable that the third coupling portion 68 having flexibility is provided when the device 10 is used as a wearable device.

The third circuit member 602 of the present embodiment works as a power device configured to supply electric power to the other circuit members such as the second circuit member 50 and the third circuit member 604. The third body 61 has a third main portion 62 configured to perform the aforementioned function of the third circuit member 602. For example, the third main portion 62 includes a power storage circuit, which receives electric power from an outside object in a non-contact manner and stores the received electric power, and a power supply circuit which supplies the stored electric power to the other circuit boards. Thus, the third main portion 62 includes various components such as an IC chip.

The third main portion 62 of the present embodiment includes the aforementioned components but does not include an electrode configured to be brought into contact with an outside object. However, the present invention is not limited thereto. For example, the third main portion 62 may further include an electrode for receiving electric power from an outside object in a contact manner. The number of the third main portion 62 of the third circuit member 602 may be two or more. The function of the third circuit member 602 of the present invention is not limited to that of the present embodiment. The structure of the third main portion 62 can be variously modified in accordance with the function of the third circuit member 602. For example, the third main portion 62 may include the main electrode 422 instead of the aforementioned components.

The third integrated-electrode portion 66 of the present embodiment is a relay portion through which electric power is transmitted to the other circuit boards. The third integrated-electrode portion 66 is formed with a third predetermined number of third electrodes 662. The third predetermined number of the present embodiment is sixteen. The third electrodes 662 are arranged in a 4×4 grid. In other words, the third electrodes 662 form a 4×4 grid array. However, the present invention is not limited thereto. For example, the number of the third electrodes 662 may be two. Thus, the third integrated-electrode portion 66 should be formed with two or more of the third electrodes 662.

The third main portion 62 is connected to the third flexible board 64. The third flexible board 64 has a three-layer structure consisting of an upper insulation layer, a wiring layer, and a lower insulation layer, where the upper insulation layer and the lower insulation layer constitute a third insulation layer 63. The wiring layer is located between the upper insulation layer and the lower insulation layer in the upper-lower direction. The wiring layer includes a third wiring 69. Thus, the third circuit member 602 is formed with the third wiring 69.

The third wiring 69 of the present embodiment includes two conductive patterns for transmitting electric power. Each of the conductive patterns of the third wiring 69 connects one of the third electrodes 662 and the third main portion 62 to each other. The third wiring 69 of the present embodiment has the aforementioned structure. However, the structure of the third wiring 69 of the present invention is not specifically limited, provided that the third wiring 69 connects the third main portion 62 to at least one of the third electrodes 662. The layer structure of the third flexible board 64 of the present invention is not specifically limited.

Figure 8:
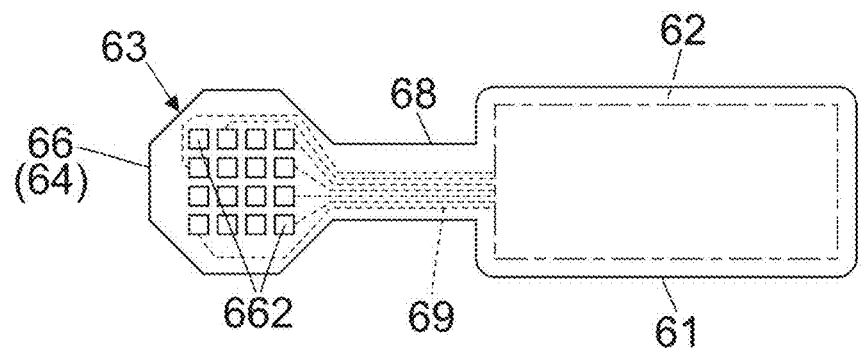
FIG. 8 is a plan view showing a remaining one of the third circuit members of the device of FIG. 4, wherein a hidden third wiring is illustrated with dashed line, and a position of the third main portion is illustrated with chain dotted lines.

Referring to FIGS. 4 and 8, the third circuit member 604 of the third circuit members 60 of the present embodiment has a structure described below.

The third circuit member 604 comprises a third body 61 and a third flexible board 64. The third body 61 is a rigid circuit board. The third flexible board 64 is a flexible circuit board which is thin and bendable. Each of the third body 61 and the third flexible board 64 extends in parallel to the XY-plane.

The third body 61 and the third flexible board 64 are coupled to each other in a horizontal direction perpendicular to the upper-lower direction. The third flexible board 64 has a third integrated-electrode portion 66 and a third coupling portion 68. The third coupling portion 68 is connected to the third integrated-electrode portion 66 in the horizontal direction and extends from the third integrated-electrode portion 66 along the horizontal direction. The third body 61 is connected to the third coupling portion 68 in the horizontal direction.

The third circuit member 604 of the present embodiment has the aforementioned basic structure. The third body 61 is a member different and distinct from the third flexible board 64. Each of the third integrated-electrode portion 66 and the third coupling portion 68 is a part of the single third flexible board 64. However, the present invention is not limited thereto. For example, the number of the third body 61 may be two or more. The third body 61 may be a part of the flexible circuit board. The third coupling portion 68 may be a rigid circuit board different and distinct from the third flexible board 64. The third coupling portion 68 may be provided as necessary. For example, it is preferable that the third coupling portion 68 having flexibility is provided when the device 10 is used as a wearable device.

The third circuit member 604 of the present embodiment uses the electric power supplied from the third circuit member 602 when it works. The third circuit member 604 works as a sensor which measures the electric pulse of the heart based on the biological signals obtained by the first circuit member 40. The third body 61 has a third main portion 62 configured to perform the aforementioned function of the third circuit member 604. For example, the third main portion 62 includes a sensor circuit formed of various components. Thus, the third main portion 62 includes various components such as an IC chip.

The third main portion 62 of the present embodiment includes the aforementioned components but does not include an electrode configured to be brought into contact with an outside object. However, the present invention is not limited thereto. For example, the third main portion 62 may further include the main electrode 422 for directly receiving biological signals. The number of the third main portion 62 of the third circuit member 604 may be two or more. The function of the third circuit member 604 of the present invention is not limited to that of the present embodiment. The structure of the third main portion 62 can be variously modified in accordance with a function of the third circuit member 604. For example, the third main portion 62 may include the main electrode 422 instead of the aforementioned components.

The third integrated-electrode portion 66 of the present embodiment is a relay portion through which the biological signals and the electric power are received and through which the measurement result is transmitted. The third integrated-electrode portion 66 is formed with a third predetermined number of third electrodes 662. The third predetermined number of the present embodiment is sixteen. The third electrodes 662 are arranged in a 4×4 grid. In other words, the third electrodes 662 form a 4×4 grid array. However, the present invention is not limited thereto. For example, the number of the third electrodes 662 may be two. Thus, the third integrated-electrode portion 66 should be formed with two or more of the third electrodes 662.

The third main portion 62 is connected to the third flexible board 64. The third flexible board 64 has a three-layer structure consisting of an upper insulation layer, a wiring layer, and a lower insulation layer, where the upper insulation layer and the lower insulation layer constitute a third insulation layer 63. The wiring layer is located between the upper insulation layer and the lower insulation layer in the upper-lower direction. The wiring layer includes a third wiring 69. Thus, the third circuit member 604 is formed with the third wiring 69.

The third wiring 69 of the present embodiment includes seven conductive patterns for transmitting the biological signals, the measurement result and the electric power. Each of the conductive patterns of the third wiring 69 connects one of the third electrodes 662 and the third main portion 62 to each other. The third wiring 69 of the present embodiment has the aforementioned structure. However, the structure of the third wiring 69 of the present invention is not specifically limited, provided that the third wiring 69 connects the third main portion 62 to at least one of the third electrodes 662. The layer structure of the third flexible board 64 of the present invention is not specifically limited.

Figure 6:
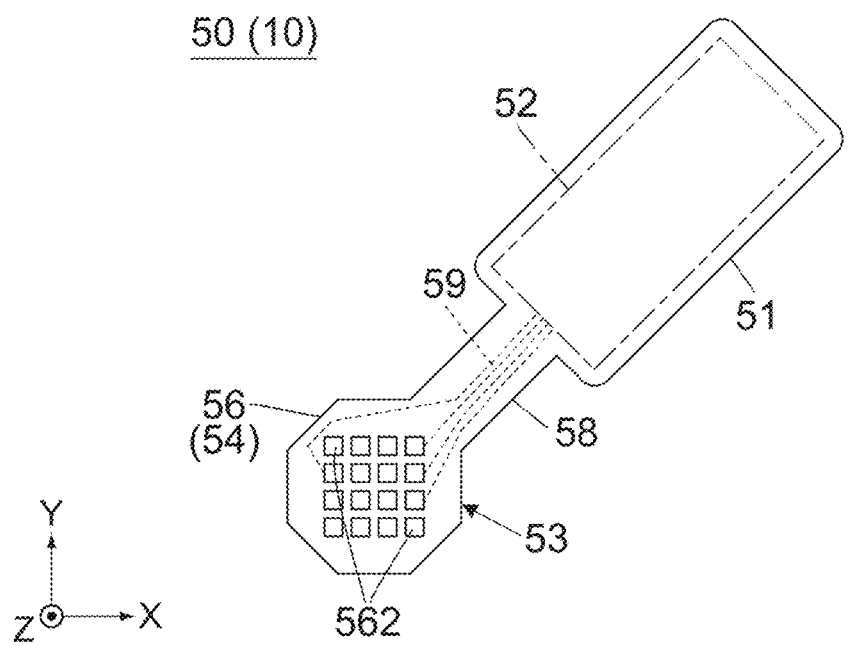
FIG. 6 is a plan view showing a second circuit member of the device of FIG. 4, wherein a hidden second wiring is illustrated with dashed line, and a position of the second main portion is illustrated with chain dotted lines.

Referring to FIGS. 4 and 6, the second circuit member 50 of the present embodiment has a structure described below.

The second circuit member 50 comprises a second body 51 and a second flexible board 54. The second body 51 is a rigid circuit board. The second flexible board 54 is a flexible circuit board which is thin and bendable. Each of the second body 51 and the second flexible board 54 extends in parallel to the XY-plane.

The second body 51 and the second flexible board 54 are coupled to each other in a horizontal direction perpendicular to the upper-lower direction. The second flexible board 54 has a second integrated-electrode portion 56 and a second coupling portion 58. The second coupling portion 58 is connected to the second integrated-electrode portion 56 in the horizontal direction and extends from the second integrated-electrode portion 56 along the horizontal direction. The second body 51 is connected to the second coupling portion 58 in the horizontal direction.

The second circuit member 50 of the present embodiment has the aforementioned basic structure. The second body 51 is a member different and distinct from the second flexible board 54. Each of the second integrated-electrode portion 56 and the second coupling portion 58 is a part of the single second flexible board 54. However, the present invention is not limited thereto. For example, the number of the second body 51 may be two or more. The second body 51 may be a part of the flexible circuit board. The second coupling portion 58 may be a rigid circuit board different and distinct from the second flexible board 54. The second coupling portion 58 may be provided as necessary. For example, it is preferable that the second coupling portion 58 having flexibility is provided when the device 10 is used as a wearable device.

The second circuit member 50 of the present embodiment uses the electric power supplied from the third circuit member 602. when it works. The second circuit member 50 works as a transmitter configured to wirelessly send the measurement result of the electric pulse of the heart measured by the third circuit member 604 to another electronic device (not shown). The second body 51 has a second main portion 52 configured to perform the aforementioned function of the second circuit member 50. For example, the second main portion 52 includes a micro controller unit (MCU) and a bluetooth low energy (BLE) unit. Thus, the second main portion 52 includes various components such as an IC chip.

The second main portion 52 of the present embodiment include the aforementioned components but does not include an electrode configured to be brought into contact with an outside object. However, the present invention is not limited thereto. For example, the second main portion 52 may further include an electrode for sending the measurement result outward via wires. The number of the second main portion 52 of the second circuit member 50 may be two or more. The function of the second circuit member 50 of the present invention is not limited to that of the present embodiment. The structure of the second main portion 52 can be variously modified in accordance with a function of the second circuit member 50. For example, the second main portion 52 may include the main electrode 422 instead of the aforementioned components.

The second integrated-electrode portion 56 of the present embodiment is a relay portion through which the measurement result and the electric power are received. The second integrated-electrode portion 56 is formed with a second predetermined number of second electrodes 562. The second predetermined number of the present embodiment is sixteen. The second electrodes 562 are arranged in a 4×4 grid. In other words, the second electrodes 562 form a 4×4 grid array. However, the present invention is not limited thereto. For example, the number of the second electrodes 562 may be two. Thus, the second integrated-electrode portion 56 should be formed with two or more of the second electrodes 562.

The second main portion 52 is connected to the second flexible board 54. The second flexible board 54 has a three-layer structure consisting of an upper insulation layer, a wiring layer, and a lower insulation layer, where the upper insulation layer and the lower insulation layer constitute a second insulation layer 53. The wiring layer is located between the upper insulation layer and the lower insulation layer in the upper-lower direction. The wiring layer includes a second wiring 59. Thus, the second circuit member 50 is formed with the second wiring 59.

The second wiring 59 of the present embodiment includes four conductive patterns for transmitting the measurement result and the electric power. Each of the conductive patterns of the second wiring 59 connects one of the second electrodes 562 and the second main portion 52 to each other. The second wiring 59 of the present embodiment has the aforementioned structure. However, the structure of the second wiring 59 of the present invention is not specifically limited, provided that the second wiring 59 connects the second main portion 52 to at least one of the second electrodes 562. The layer structure of the second flexible board 54 of the present invention is not specifically limited.

Referring to FIG. 1, the device 10 of the present embodiment is an assembly of the four circuit members described above and works as a single electronic circuit for measuring the biological signals. However, the present invention is not limited thereto. For example, the device 10 is not limited to the measurement device of the biological signals but can be used for various purposes. Moreover, the device 10 may include two or more electric circuits which work independently from each other. The number of the circuit members and the structure of each of the circuit members may be designed in accordance with the use of the device 10. According to the present embodiment, the device 10 can be improved in flexibility of design.

For example, the main electrode 422 may be provided on one of the second body 51 of the second circuit member 50 and the third bodies 61 of the third circuit members 60 instead of the first bodies 41 of the first circuit member 40. In this instance, each of the first bodies 41 may be provided with components such as an IC chip. Thus, at least one of the first main portions 42, the second main portion 52 and the third main portions 62 may include the main electrode 422, and at least one of the first main portions 42, the second main portion 52 and the third main portions 62 may include components other than the main electrode 422.

Figure 3:
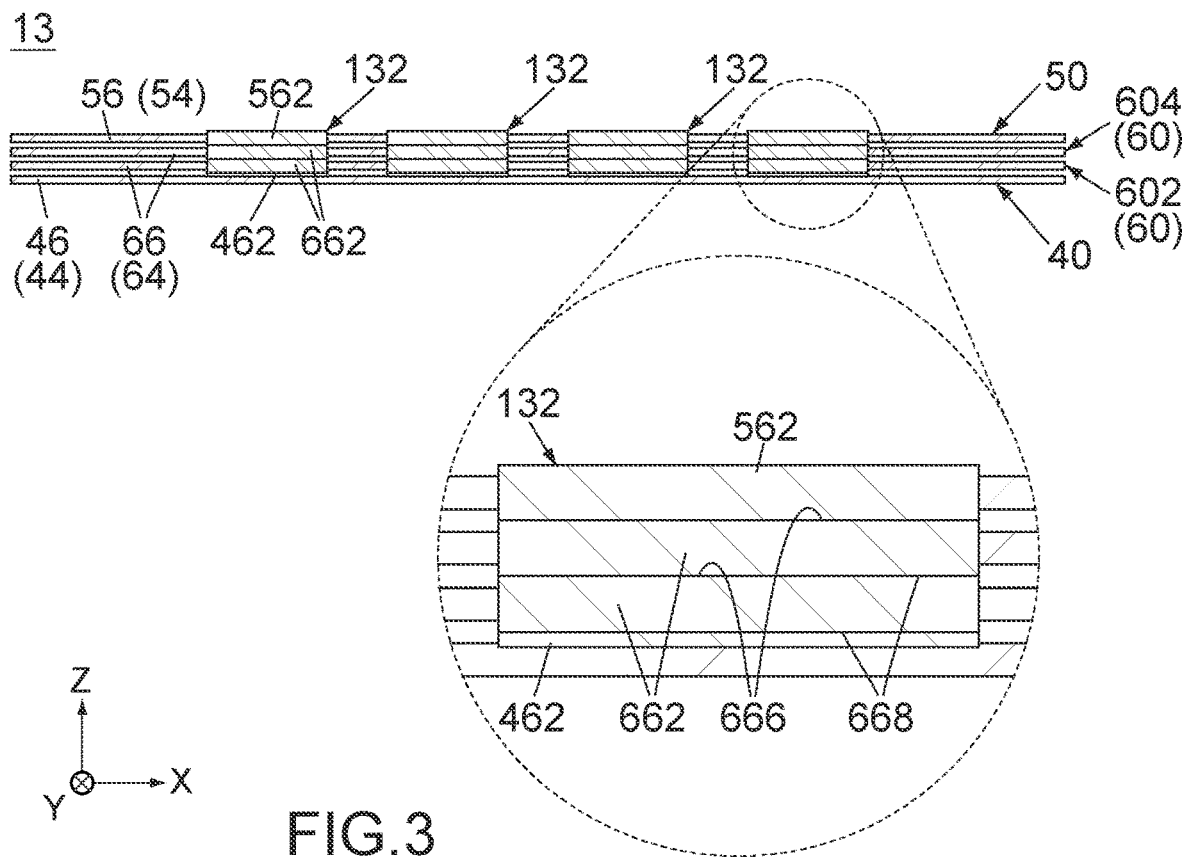
FIG. 3 is an edge view showing an integrated-electrode portion of the device of FIG. 2, taken along line III-III, wherein a part of the device enclosed by dashed line is enlarged and illustrated.

Referring to FIG. 2 together with FIG. 3, the first integrated-electrode portion 46 of the first circuit member 40, the second integrated-electrode portion 56 of the second circuit member 50 and the third integrated-electrode portions 66 of the third circuit members 60 are stacked on each other in the upper-lower direction so that the device 10 is assembled. Thus, the first integrated-electrode portion 46, the second integrated-electrode portion 56 and the third integrated-electrode portions 66 lie over each other in the upper-lower direction. For example, when the device 10 is used without being enclosed in a sheet-like member described later, the first integrated-electrode portion 46, the second integrated-electrode portion 56 and the third integrated-electrode portions 66 may be fixed to each other by using a fixation member such as an adhesive.

According to the present embodiment, the whole first integrated-electrode portion 46, the whole second integrated-electrode portion 56 and the whole third integrated-electrode portion 66 completely cover each other in the upper-lower direction so that one integrated-electrode portion 13 is formed. The integrated-electrode portion 13 works as a relay portion through which the aforementioned various signals of the circuit structure 12 are transmitted.

The first integrated-electrode portion 46, the second integrated-electrode portion 56 and the third integrated-electrode portions 66 of the present embodiment have regular polygon shapes same as each other in the XY-plane and are thereby easily positioned to each other in the XY-plane. However, the present invention is not limited thereto. For example, the first integrated-electrode portion 46, the second integrated-electrode portion 56 and the third integrated-electrode portions 66 may have circular shapes in the XY-plane or may have shapes different from each other. The first integrated-electrode portion 46, the second integrated-electrode portion 56 and the third integrated-electrode portions 66 may partially lie over each other in the upper-lower direction. Thus, the first integrated-electrode portion 46, the second integrated-electrode portion 56 and the third integrated-electrode portion 66 may, at least in part, lie over each other in the upper-lower direction.

Referring to FIG. 3, the first integrated-electrode portion 46 is located at the lowermost layer of the integrated-electrode portion 13. The second integrated-electrode portion 56 is located at the uppermost layer of the integrated-electrode portion 13. The two third integrated-electrode portions 66 are located between the first integrated-electrode portion 46 and the second integrated-electrode portion 56 in the upper-lower direction. According to the present embodiment, the third integrated-electrode portion 66 of the third circuit member 604 is located over the third integrated-electrode portion 66 of the third circuit member 602. However, the present invention is not limited thereto. For example, positional relation between two or more of the third integrated-electrode portions 66 in the upper-lower direction is not specifically limited.

Each of the first electrodes 462 of the first integrated-electrode portion 46 is exposed upward. Each of the second electrodes 562 of the second integrated-electrode portion 56 is exposed downward. Each of the second electrodes 562 of the present embodiment is also exposed upward. Each of the third electrodes 662 of the third integrated-electrode portions 66 has an upper end surface 666 exposed upward and a lower end surface 668 exposed downward, the upper end surface 666 and the lower end surface 668 being electrically connected with each other.

Referring to FIG. 3 together with FIG. 4, in the present embodiment, the first predetermined number which is the number of the first electrodes 462, the second predetermined number which is the number of the second electrodes 562 and the third predetermined number which is the number of the third electrodes 662 of each of the third integrated-electrode portions 66 are equal to each other. According to the present embodiment, the first electrodes 462 are arranged in a predetermined electrode arrangement, or a 4×4 grid arrangement, the second electrodes 562 are arranged in this predetermined electrode arrangement, and the third electrodes 662 of each of the third integrated-electrode portions 66 are arranged in this predetermined electrode arrangement. The first electrodes 462 are connected to the second electrodes 562, respectively, via the third electrodes 662 of each of the third integrated-electrode portions 66, respectively.

Referring to FIG. 3 together with FIG. 2, according to the present embodiment, each of the first electrodes 462 forms one of connection electrodes 132 together with two of the third electrodes 662 and one of the second electrodes 562 located just above the first electrode 462. According to the present embodiment, the sixteen connection electrodes 132 are formed and are arranged in a 4×4 grid. Each of the connection electrodes 132 has an upper end surface and a lower end surface which are electrically connected with each other. The first main portions 42, the second main portion 52 and the third main portions 62 are electrically connected with each other via the first wiring 49 (see FIG. 5), the second wiring 59 (see FIG. 6), the third wirings 69 (see FIGS. 7 and 8) and the connection electrodes 132.

According to the present embodiment, the first main portions 42, the second main portion 52 and the third main portions 62 can be electrically connected with each other via the connection electrodes 132. Each of the first main portions 42, the second main portion 52 and the third main portions 62 can be provided with an electronic circuit including various components such as an IC chip and can be provided with the main electrode 422 connectable to an object located outside the device 10. Thus, the device 10 of the present embodiment can be used as an electronic device which comprises three or more electronic circuits connected to each other.

The connection electrodes 132 of the present embodiment include non-used electrodes which are not used for electrical connection between the first main portions 42, the second main portion 52 and the third main portions 62. For example, the four connection electrodes 132 located at the center of the 4×4 grid arrangement are the non-used electrodes. These non-used electrodes do not need to be formed. More specifically, the first electrodes 462, the second electrodes 562 and the third electrodes 662 of the non-used electrodes do not need to be formed. However, from a viewpoint of easy and general-purpose formation of the first electrodes 462, the second electrodes 562 and the third electrodes 662, the non-used electrodes such as those of the present embodiment may be formed. Thus, at least one of the first electrodes 462 and at least one of the second electrodes 562 should be connected to each other via a predetermined one of the third electrodes 662.

Referring to FIG. 3, each of the first electrodes 462 of the present embodiment is gold flash plated and projects upward beyond an upper surface of the first integrated-electrode portion 46. Each of the third electrodes 662 of the present embodiment projects downward beyond a lower surface of the third integrated-electrode portion 66 and projects upward beyond an upper surface of the third integrated-electrode portion 66. Each of the second electrodes 562 of the present embodiment projects downward beyond a lower surface of the second integrated-electrode portion 56 and projects upward beyond an upper surface of the second integrated-electrode portion 56. According to the aforementioned structure, each of the first electrodes 462 can be reliably connected to a predetermined one of the second electrodes 562 via predetermined two of the third electrodes 662.

However, the present invention is not limited thereto. For example, the upper end of each of the second electrodes 562 may be located below the upper surface of the second integrated-electrode portion 56.

According to the present embodiment, each of the first integrated-electrode portion 46, the second integrated-electrode portion 56 and the third integrated-electrode portions 66 which lie over each other is formed in a flexible circuit board. The part in which the flexible circuit boards lie over each other can be reduced in height by making them thinner.

Referring to FIG. 2, the first bodies 41, the second body 51 and the third bodies 61, which are formed with the first main portions 42, the second main portion 52 and the third main portions 62, respectively, are connected to the first coupling portions 48, the second coupling portion 58 and the third coupling portions 68, respectively, which radially extend from the integrated-electrode portion 13 along various orientations different from each other. Thus, the first bodies 41, the second body 51 and the third bodies 61 are apart from each other when seen along the upper-lower direction. In other words, the first bodies 41, the second body 51 and the third bodies 61 do not lie over each other in the upper-lower direction. Therefore, even in an instance where each of the first main portions 42, the second main portion 52 and the third main portions 62 is provided with various components such as an IC chip, the height of the device 10 is not substantially changed as a whole.

As can be seen from the explanation described above, the present embodiment provides the device 10 which comprises stacked three or more of the circuit members and can be reduced in height. In other words, the device 10 of the present embodiment is a thin electronic device. In addition, because the connection electrodes 132, which connect the first main portions 42, the second main portion 52 and the third main portions 62 with each other, are integrated in the middle of the device 10 in the XY-plane, the device 10 can be reduced in size in the XY-plane in spite of various circuit members provided thereto.

The circuit structure 12 of the present invention may be solely used as the device 10 as previously described. Instead, the circuit structure 12 may be used under a state where the circuit structure 12 is enclosed in a flexible sheet-like member or a hard protection member such as those of modifications described below.

Figure 9:
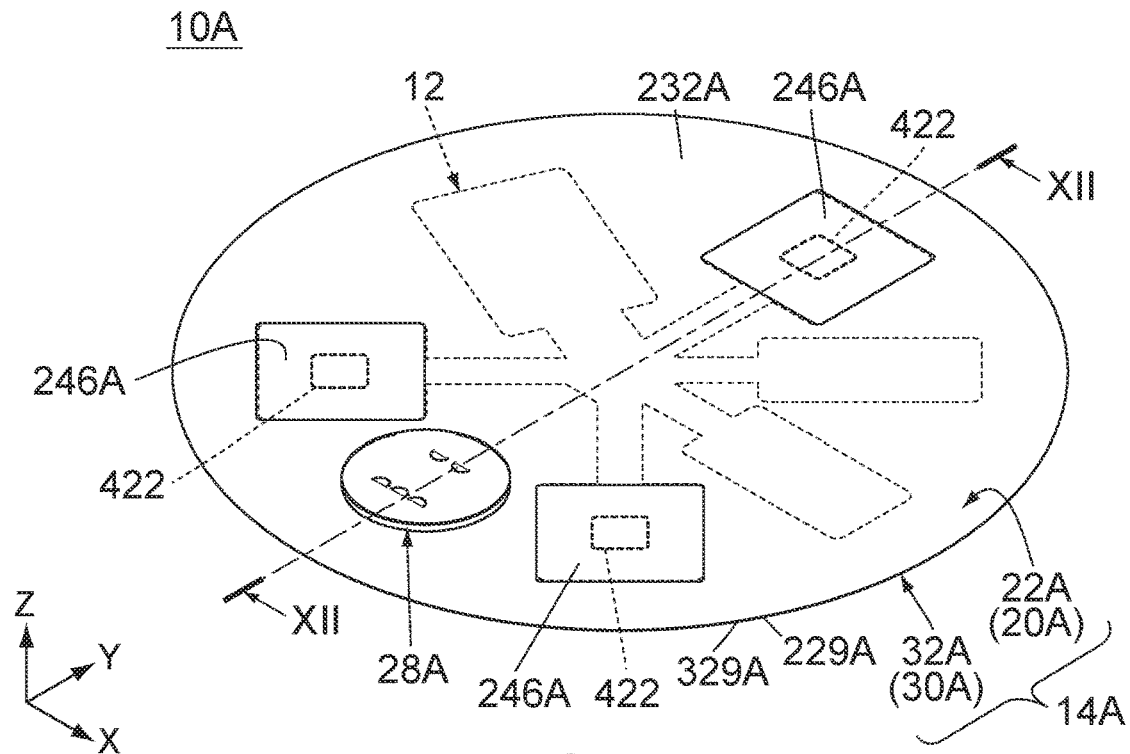
FIG. 9 is a perspective view showing a first modification of the device of FIG. 1, wherein an outline of a hidden circuit structure is illustrated with dashed line.
Figure 10:
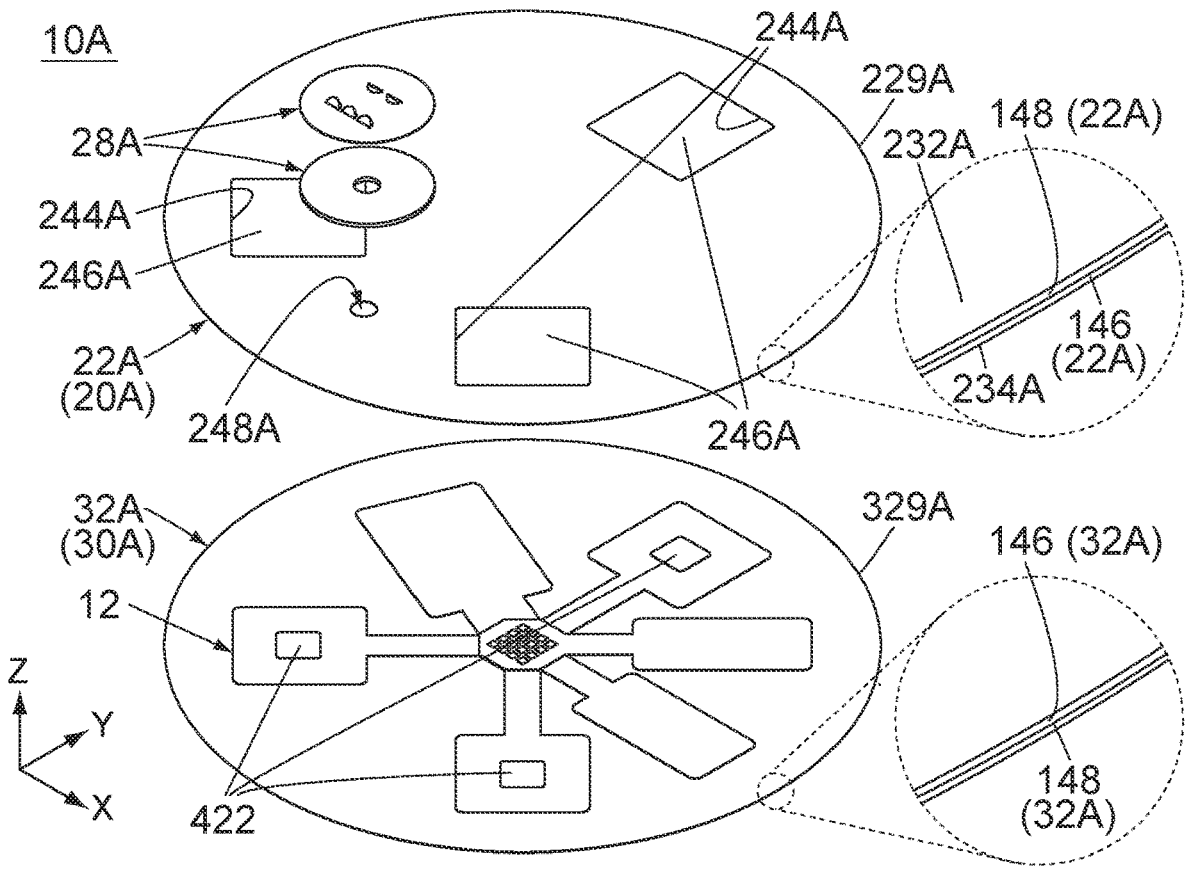
FIG. 10 is an exploded, perspective view showing the device of FIG. 9, wherein a part of a first film enclosed by dashed line and a part of a second film enclosed by dashed line are enlarged and illustrated, and valves of an air valve are open.

Referring to FIGS. 9 and 10, a device 10A according to a first modification comprises a sealing member 14A in addition to the circuit structure 12. The circuit structure 12 has the already described structure and can be variously modified as already described. The sealing member 14A entirely encloses the circuit structure 12 therewithin and protects the circuit structure 12 from an external environment. Thus, the circuit structure 12 is shut in the sealing member 14A.

The sealing member 14A of the present modification is a flexible sheet-like member. The sealing member 14A comprises a first sealing member 20A and a second sealing member 30A. Thus, the device 10A comprises the first sealing member 20A and the second sealing member 30A in addition to the circuit structure 12. The device 10A of the present modification comprises only the circuit structure 12, the first sealing member 20A and the second sealing member 30A. However, the present invention is not limited thereto, but the device 10A may further comprise another member.

Referring to FIG. 10, the first sealing member 20A of the present modification is formed of, as a base thereof, a first film 22A which is an insulation film. In other words, the first sealing member 20A comprises, as a base of the first sealing member 20A, the first film 22A formed of a film. The first film 22A of the present modification is a thin, circular sheet and is bendable. The first film 22A extends in parallel to the XY-plane. The first film 22A has a peripheral edge 229A in the XY-plane. However, the present invention is not limited to the present modification. For example, the first film 22A may have a rectangular shape. The first sealing member 20A may comprise, as a base thereof, a rigid protection member (not shown) made of insulator instead of the first film 22A.

Figure 12:
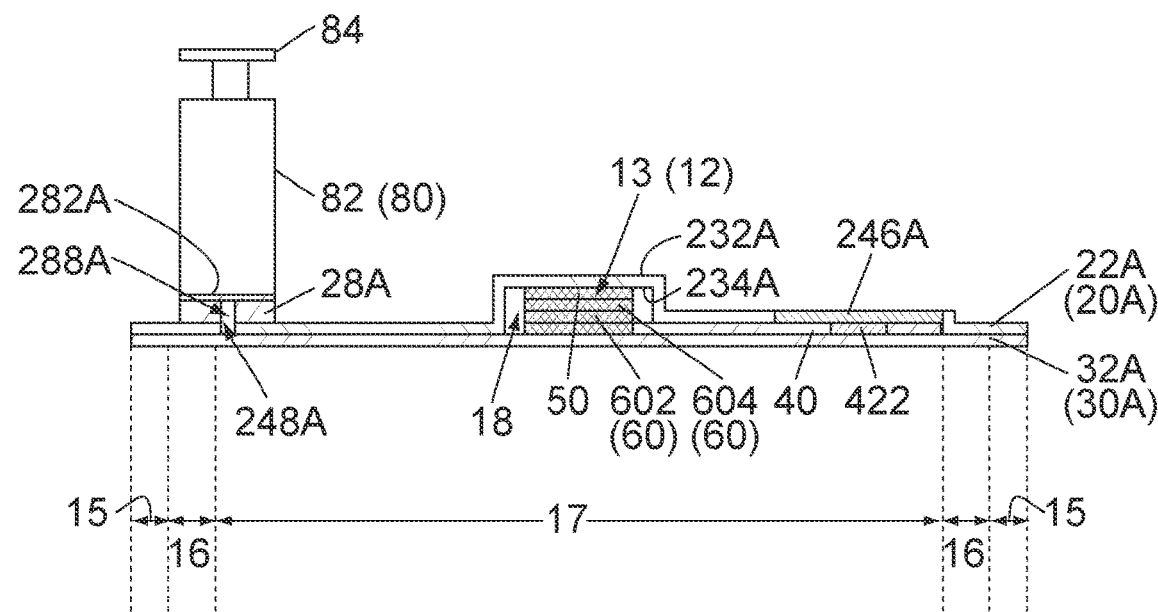
FIG. 12 is a schematic, edge view showing the device of FIG. 9, taken along line XII-XII, wherein the inner structure of the device is merely schematically illustrated, the size and arrangement of each member are not equal to the actual size and arrangement thereof, and a side surface of an instrument for vacuuming is illustrated.

Referring to FIGS. 9 and 12, the first film 22A has an outer surface 232A and an inner surface 234A. The outer surface 232A is an upper surface of the first film 22A. The inner surface 234A is a lower surface of the first film 22A.

Referring to FIG. 10, the second sealing member 30A of the present modification is formed of, as a base thereof, a second film 32A which is an insulation film. In other words, the second sealing member 30A comprises, as a base of the second sealing member 30A, the second film 32A formed of a film. The second film 32A of the present modification is a thin, circular sheet and is bendable. The second film 32A extends in parallel to the XY-plane. The second film 32A has a peripheral edge 329A in the XY-plane. However, the present invention is not limited to the present modification. For example, the second sealing member 30A may have a rectangular shape. The second sealing member 30A may comprise, as a base thereof, a rigid protection member (not shown) made of insulator instead of the second film 32A. However, in an instance where one of the first sealing member 20A and the second sealing member 30A comprises, as a base thereof, a rigid member, a remaining one of them is preferred to comprise, as a base thereof, a bendable insulation film.

Referring to FIG. 9 together with FIG. 10, the first film 22A and the second film 32A of the present modification lie over each other so that the position of the peripheral edge 229A and the position of the peripheral edge 329A are aligned with each other in the XY-plane. However, the present invention is not limited thereto. For example, the size of the first film 22A in the XY-plane and the size of the second film 32A in the XY-plane may be different from each other.

Referring to FIG. 10, each of the first film 22A and the second film 32A of the present modification comprises two layers consisting of a meltable layer 146 which is meltable by heat-treatment and an unmeltable layer 148 which is not meltable by heat-treatment. For example, the meltable layer 146 is made of polyethylene, and the unmeltable layer 148 is made of nylon. The meltable layer 146 of the first film 22A is located under the unmeltable layer 148. The meltable layer 146 of the second film 32A is located over the unmeltable layer 148.

According to the aforementioned structure, the two meltable layers 146 of the first film 22A and the second film 32A can be fused to each other while the unmeltable layers 148 are maintained. Thus, the first film 22A and the second film 32A can be bonded together by fusing. However, the present invention is not limited thereto. Each of the first film 22A and the second film 32A may have any structure, provided that it is in accordance with a forming method of the device 10A. For example, the first film 22A and the second film 32A may be bonded together by using a fixing member such as an adhesive. In this instance, each of the first film 22A and the second film 32A may comprise only one layer which is the unmeltable layer 148. Or else, each of the first film 22A and the second film 32A may comprise three or more layers.

The first film 22A is formed with three openings 244A and a valve opening 248A. Each of the openings 244A of the present modification has a rectangular shape in the XY-plane and passes through the first film 22A in the upper-lower direction. The valve opening 248A of the present modification has a small circular shape in the XY-plane and passes through the first film 22A in the upper-lower direction. Each of the openings 244A and the valve opening 248A as described above can be formed by a forming method such as laser irradiation. However, the present invention is not limited thereto. For example, the shape and the size in the XY-plane of each of the openings 244A and the valve opening 248A are not specifically limited.

The first sealing member 20A of the present modification comprises three conductive portions 246A each made of conductor such as metal and an air valve 28A in addition to the first film 22A.

For example, the conductive portions 246A of the present modification can be formed as described below. First, the first film 22A is formed with three openings 244A. Then, each of the openings 244A is filled with conductive paste which is spread on one of opposite surfaces of the first film 22A by using a proper mask and a doctor blade. Then, the first film 22A is heated so that the conductive paste is hardened. Then, each of the openings 244A is filled with conductive paste which is spread on a remaining one of the opposite surfaces of the first film 22A by using a proper mask and the doctor blade. Then, the first film 22A is heated so that the conductive paste is hardened. The three conductive portions 246A are formed of the conductive paste as a result of the aforementioned twice heat-treatments.

The conductive portions 246A of the present modification are formed as described above and entirely cover the openings 244A. However, the present invention is not limited thereto. For example, the conductive portions 246A may be formed by plating or by ink-jetting. Each of the conductive portions 246A may be formed of metal foil which is laminated on the outer surface 232A or the inner surface 234A of the first film 22A so as to cover the whole opening 244A. Each of the conductive portions 246A may partially protrude downward.

The conductive portions 246A are provided so as to correspond to the openings 244A, respectively. The openings 244A are provided so as to correspond to the main electrodes 422, respectively. Thus, the number of the conductive portions 246A is equal to the number of the openings 244A, and the number of the openings 244A is equal to the number of the main electrodes 422.

Figure 11:
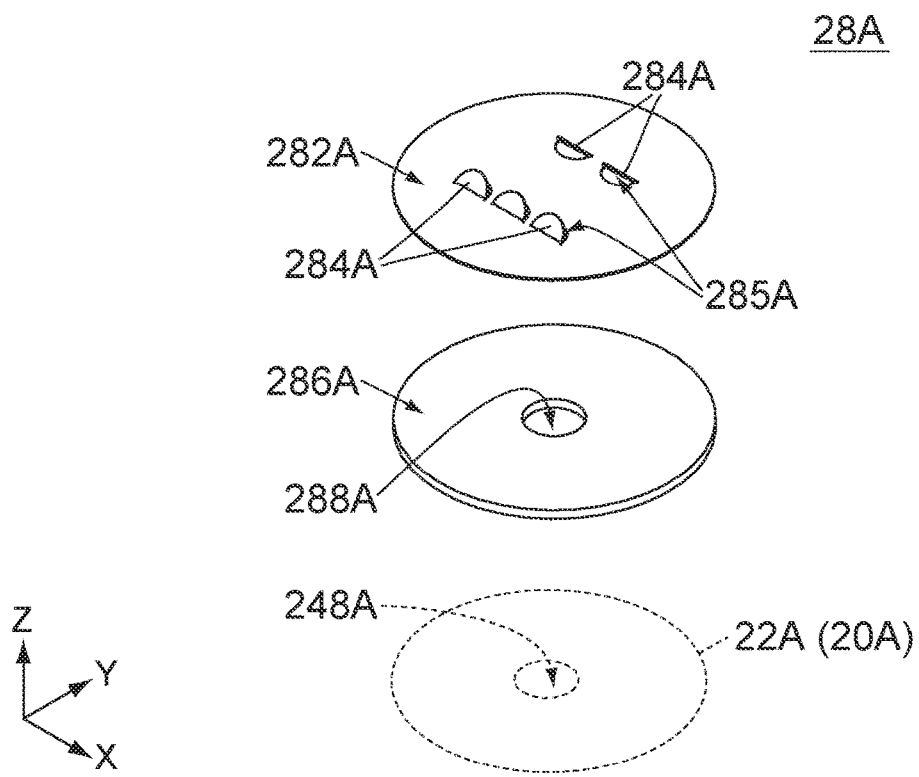
FIG. 11 is an exploded, perspective view showing the air valve of FIG. 10, wherein a part of the first film is illustrated with dashed line.

Referring to FIG. 11 together with FIG. 10, the air valve 28A of the present modification comprises a cover portion 282A formed of a thin insulation film and a base portion 286A made of insulator. The base portion 286A is formed with a passing hole 288A. The passing hole 288A passes through the base portion 286A in the upper-lower direction. The cover portion 282A is formed with five valves 284A and five cuts 285A which correspond to the valves 284A, respectively. Each of the cuts 285A passes through the cover portion 282A in the upper-lower direction. The valves 284A and the cuts 285A are located inward of an outer circumference of the cover portion 282A in the XY-plane.

Referring to FIG. 11 together with FIG. 9, the cover portion 282A is adhered to and fixed on an upper surface of the base portion 286A. In particular, the outer circumference of the cover portion 282A in the XY-plane is tightly adhered to the upper surface of the base portion 286A throughout its entire circumference. In contrast, an inner part of the cover portion 282A, which is located inward of the outer circumference of the cover portion 282A in the XY-plane, can be pulled away from the upper surface of the base portion 286A. Thus, a passage which allows air to pass therethrough can be formed between the passing hole 288A and each of the cuts 285A. The base portion 286A has a lower surface which is adhered to and fixed on the first film 22A in such a way that the passing hole 288A communicates with the valve opening 248A of the first film 22A.

The air valve 28A can take either an open state shown in FIG. 11 or a closed state shown in FIG. 9. When the air valve 28A takes the open state, each of the valves 284A is apart from the corresponding cut 285A. When the air valve 28A takes the closed state, each of the valves 284A completely covers the corresponding cut 285A. When the air valve 28A takes the open state, an air passage via the air valve 28A is formed between the inside and the outside of the device 10A. When the air valve 28A takes the closed state, the inside of the device 10A is shut off from the outside of the device 10A.

The device 10A of the present modification is formed via four steps consisting of a preparing step, a stacking step, a shutting-in step and a vacuuming step. However, the present invention is not limited thereto, but the forming method of the device 10A can be modified as necessary. Hereafter, explanation will be made about an example of the forming method of the device 10A of the present modification.

Referring to FIG. 10, first, in the preparing step, the first sealing member 20A, the second sealing member 30A and the circuit structure 12 are prepared. The first circuit member 40, the second circuit member 50 and the third circuit members 60 of the-thus prepared circuit structure 12 are not fixed to each other.

Then, in the stacking step, the first sealing member 20A, the circuit structure 12 and the second sealing member 30A are stacked on each other in this order from top to bottom along the upper-lower direction. Meanwhile, the circuit structure 12 are arranged so that the single integrated-electrode portion 13 (see FIG. 1) is formed. The three conductive portions 246A are arranged so that they face the three main electrodes 422, respectively, in the upper-lower direction. In addition, the first film 22A and the second film 32A are arranged so that two of the meltable layers 146 (see FIG. 6) thereof face each other in the upper-lower direction.

Then, in the shutting-in step, heat-sealing is applied to the first film 22A and the second film 32A. In detail, parts of the two meltable layers 146, which are located at outer circumferences of the first film 22A and the second film 32A in the XY-plane, are welded to each other via heat-sealing. Referring to FIG. 12, as a result of the heat-sealing, the device 10A with a seal portion 15 is formed. The device 10A has an inner space which is enclosed by the first sealing member 20A and the second sealing member 30A and which is shut off from the outside of the device 10A except for the air valve 28A.

As described above, the first film 22A and the second film 32A of the present modification are bonded together by heat-sealing. However, the present invention is not limited thereto. For example, the first film 22A and the second film 32A can be bonded together by various methods such as high frequency, ultrasonic, laser or adhesive.

Then, in the vacuuming step, the inside of the device 10A is vacuumed.

According to the present modification, the air valve 28A and an instrument 80 are used for discharging the air of the inside of the device 10A. The instrument 80 of the present modification is a syringe-type piston pump. The instrument 80 comprises a syringe 82 and a plunger 84. The syringe 82 has a lower end which has a ring shape in the XY-plane. The ring shape of the syringe 82 corresponds to the outer circumference of the cover portion 282A of the air valve 28A.

In the vacuuming step, first, the lower end of the syringe 82 is pressed against the upper surface of the cover portion 282A. Then, the plunger 84 is pulled upward. Consequently, the air valve 28A takes the open state, and an air passage is formed between the inside of the device 10A and the inside of the syringe 82. The air in the inside of the device 10A is discharged into the inside of the syringe 82 through the passing hole 288A and the cuts 285A (see FIG. 11) of the air valve 28A. As a result, air pressure of the inside of the device 10A is gradually lowered. When air pressure of the inside of the device 10A becomes low pressure close to that of a vacuum, the vacuuming by using the instrument 80 is stopped. At that time, the device 10A has been fabricated.

When the vacuuming is stopped, the valves 284A (see FIG. 11) of the air valve 28A cover the cuts 285A (see FIG. 11) because of air pressure difference between air pressure of the inside of the device 10A and the atmospheric pressure, and thereby the air valve 28A takes the closed state. As a result, air pressure of the inside of the device 10A is kept to low pressure. Thus, the device 10A is formed with a closed space 18 which is shut off from the outside and has the low pressure.

Upon vacuuming, the device 10A is formed with a contact portion 16 and an inner portion 17. The contact portion 16 is a part of the device 10A where the first film 22A and the second film 32A are in close contact with each other. The inner portion 17 is a part of the device 10A for accommodating the circuit structure 12. The contact portion 16 illustrated in FIG. 12 is formed inward of the seal portion 15 in the XY-plane. The inner portion 17 illustrated in FIG. 12 is formed inward of the contact portion 16 in the XY-plane. The seal portion 15 of the present modification is formed with a seal trace (not shown) which is a trace where the first film 22A and the second film 32A are welded to each other by heat-treatment. However, the present embodiment is not limited thereto. For example, the seal trace may be an adhesion trace.

The seal portion 15 of the present modification surrounds the contact portion 16 and the inner portion 17 throughout their entire circumference in the XY-plane. The contact portion 16 of the present modification surrounds the inner portion 17 throughout its entire circumference in the XY-plane. The closed space 18 is enclosed by the inner portion 17. However, the present invention is not limited thereto. For example, the contact portion 16 may be formed on a necessary part in accordance with the forming method of the device 10A. For example, the contact portion 16 may be partially formed or may not be formed at all.

The closed space 18, which is formed as described above, is enclosed by the first sealing member 20A and the second sealing member 30A and is shut off from an outer space outside the device 10A. The first film 22A and the second film 32A of the present modification are seamlessly bonded together at the seal portion 15. In addition, the contact portion 16 is located inward of the seal portion 15 in the XY-plane and blocks air which might flow between the inside and the outside of the closed space 18. Thus, air pressure of the closed space 18 is kept to low pressure lower than the atmospheric pressure.

Each of the first circuit member 40, the second circuit member 50 and the third circuit members 60 is shut in the closed space 18 which is kept to the aforementioned low pressure. As a result, degradation of the metal members due to oxidation can be reduced. Moreover, a contact force is generated between each of the conductive portions 246A and the corresponding main electrode 422 because of air pressure difference between the inside and the outside of the closed space 18. This contact force presses each of the conductive portions 246A and the corresponding main electrode 422 against each other. Therefore, the contact between each of the conductive portions 246A and the corresponding main electrode 422 can be securely kept without using a fixing member such as an adhesive.

Referring to FIG. 12 together with FIG. 3, the first integrated-electrode portion 46, the second integrated-electrode portion 56 and the third integrated-electrode portions 66 of the integrated-electrode portion 13 are pressed against each other and are fixed to each other by a similar contact force. Consequently, at least one of the first electrodes 462 and at least one of the second electrodes 562 are pressed against a predetermined one of the third electrodes 662 to be connected to each other. According to the present modification, the contact between the first electrodes 462, the second electrodes 562 and the third electrodes 662 can be securely kept without using a fixing member such as an adhesive.

Referring to FIG. 12, a lower surface of each of the conductive portions 246A is located in the closed space 18 and is in contact with the corresponding main electrode 422. On the other hand, an upper surface of each of the conductive portions 246A is located outside the device 10A. In other words, each of the conductive portions 246A is in contact with the corresponding main electrode 422 in the closed space 18 and is partially exposed to the outer space located outside the device 10A.

If the conductive portions 246A and the main electrodes 422 are not provided, electronic circuits formed in the circuit structure 12 need to obtain biological signals of a subject with no contact with the subject. The electronic circuits need to obtain biological signals of the subject by, for example, contactless communication. However, weak biological signals are difficult to accurately obtain by contactless communication. In contrast, according to the present modification, biological signals can be accurately obtained via the conductive portions 246A which are in contact with a skin of the subject. In particular, according to the present modification, biological signals caused by the electric pulse of the heart of the subject can be accurately obtained via the three conductive portions 246A which are in contact with the chest of the subject.

Summarizing the explanation described above, the first sealing member 20A and the second sealing member 30A of the device 10A of the present modification lie over each other and are in contact with each other while the circuit structure 12 is sandwiched therebetween. Each of the first sealing member 20A and the second sealing member 30A of the present modification is basically formed of a film. Moreover, the size (thickness) of the circuit structure 12 in the upper-lower direction can be reduced as previously described, so that the thickness of the entire device 10A can be made extremely thin. Thus, the present modification provides the device 10A which can be reduced in thickness.

According to the present modification, each of the first circuit member 40, the second circuit member 50 and the third circuit members 60 can be easily taken out from the closed space 18 by cutting off the seal portion 15. Thus, according to the present modification, the members can be easily collected separately and can be reused.

Each of the first sealing member 20A and the second sealing member 30A is preferred to have various barrier properties such as a barrier property against oxygen and a barrier property against water vapor. More specifically, each of the first film 22A and the second film 32A is preferred to comprise a layer made of high barrier material which is material having a high barrier property.

According to the present modification, the simple instrument 80 can be used for easy vacuuming. The vacuuming by the instrument 80 can be repeatedly performed. For example, even when air pressure of the closed space 18 becomes higher during use of the device 10A, the instrument 80 can be used for vacuuming again. As a result, the aforementioned contact force can be kept. However, the present invention is not limited thereto, but the forming method of the device 10A can be modified as necessary. For example, the structure of the instrument 80 is not specifically limited, provided that it can be used for vacuuming.

The vacuuming with use of the instrument 80 such as that of the present modification is preferable from a viewpoint of easy fabrication of the device 10A and maintenance of the closed space 18. However, during the vacuuming with use of the instrument 80, a close contact part between the first film 22A and the second film 32A is not only formed at the contact portion 16 but also sometimes formed in the closed space 18. The thus-formed close contact part might block an air passage in the device 10A. As a result, air pressure of the closed space 18 might be insufficiently lowered. As a solution of this problem, the second film 32A may be embossed so that the air passage is reliably maintained. Or instead of embossing the second film 32A, an additional embossed film (not shown) may be arranged between the first film 22A and the second film 32A.

Instead of the illustrated instrument 80, a commercially available desktop vacuum packaging machine (not shown) may be used for sealing and vacuuming. As a further alternative, the members of the device 10A may be arranged in a chamber (not shown) so that vacuuming is performed simultaneously with heat-sealing. According to this forming method, the second film 32A does not need to be embossed. Nor does the additional embossed film (not shown) need to be provided.

Figure 13:
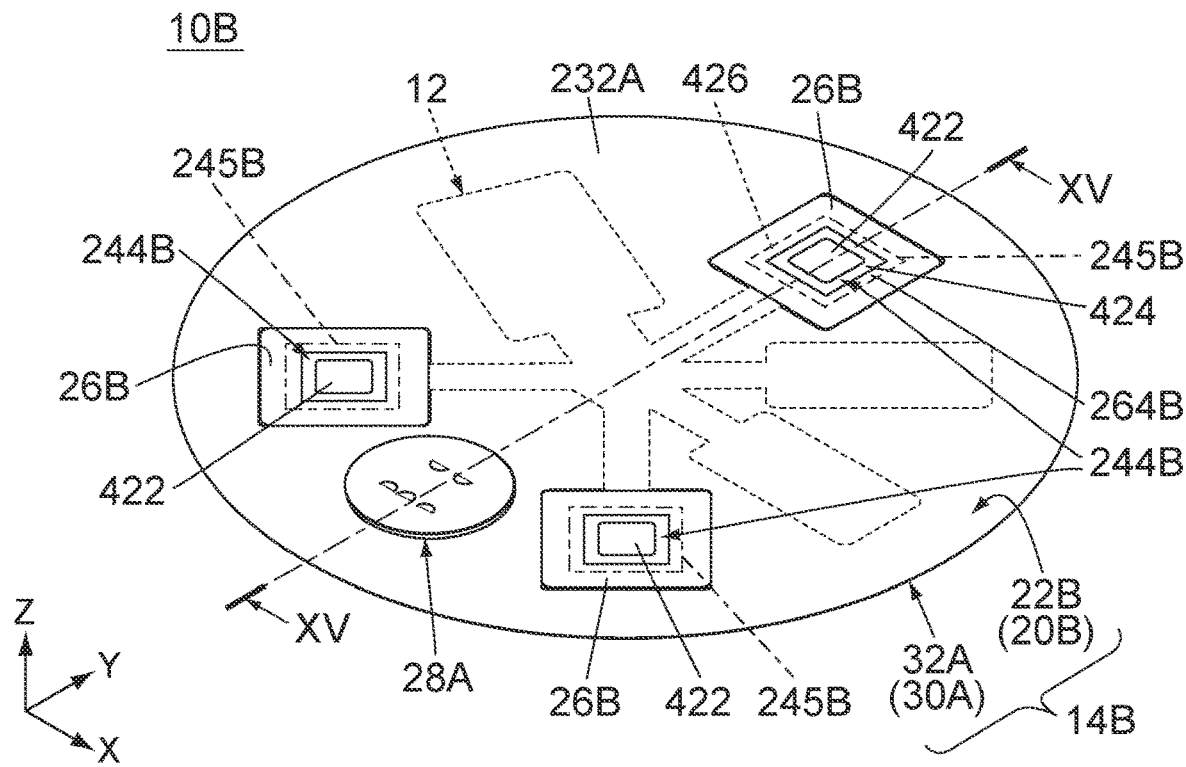
FIG. 13 is a perspective view showing a second modification of the device of FIG. 1, wherein an outline of the hidden circuit structure is illustrated with dashed line, and outlines of hidden edge portions of openings of a first film are illustrated with chain dotted lines.

Comparing FIG. 13 with FIG. 9, a device 10B according to a second modification comprises the circuit structure 12 and the second sealing member 30A same as those of the device 10A. In addition, the device 10B comprises a first sealing member 20B different from the sealing member 14A of the device 10A. Thus, the device 10B comprises a sealing member 14B consisting of the first sealing member 20B and the second sealing member 30A.

Figure 14:
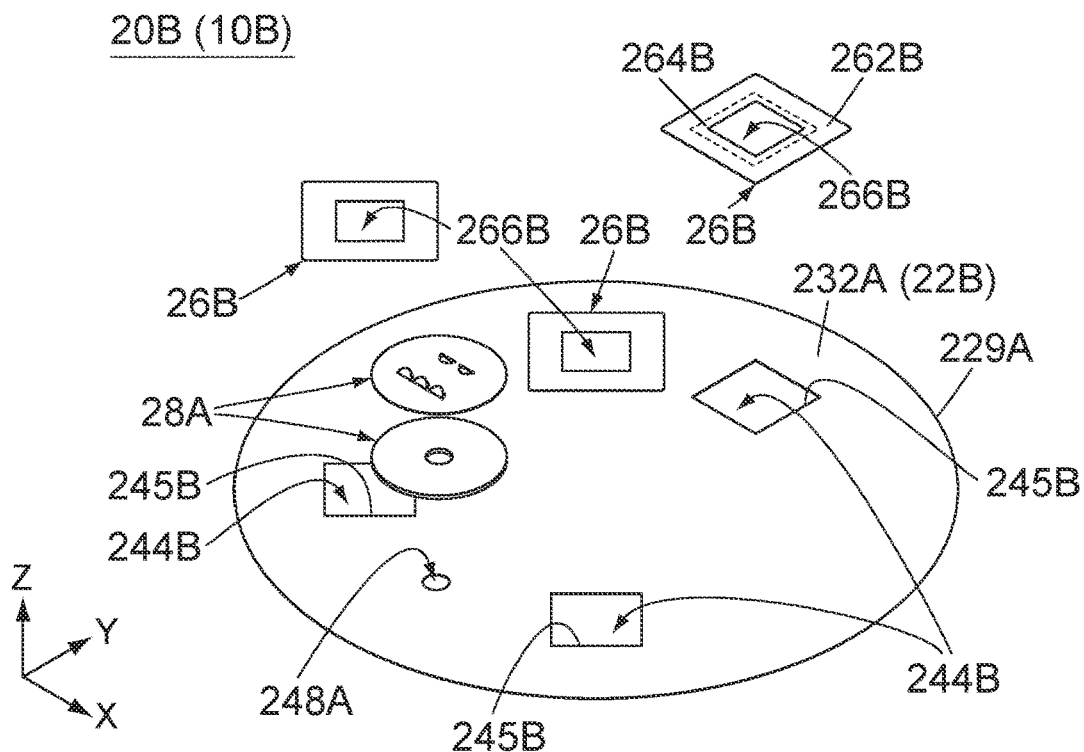
FIG. 14 is an exploded, perspective view showing a first sealing member of the device of FIG. 13, wherein a boundary between a film-seal portion and a circuit-seal portion of one of frame films are illustrated with dashed line, and the valves of the air valve are open.

Comparing FIG. 14 with FIG. 10, the first sealing member 20B comprises, as a base of the first sealing member 20B, a first film 22B formed of a film similarly to the first sealing member 20A. The first film 22B is formed with three openings 244B. Each of the openings 244B is formed with an edge portion 245B in the XY-plane. The edge portion 245B of each of the openings 244B forms a closed path. In other words, each of the openings 244B is surrounded by the edge portion 245B which forms the closed path. Each of the openings 244B has a rectangular shape which is smaller than the opening 244A in the XY-plane. However, each of the openings 244B is not provided with a portion such as the conductive portion 246A which covers the opening 244B. Except for the aforementioned differences, the first film 22B has a structure similar to that of the first film 22A. For example, the three openings 244B are provided so as to correspond to the three main electrodes 422, respectively. The number of the openings 244B is not limited to three but should be equal to the number of the main electrodes 422.

The first sealing member 20B comprises the air valve 28A same as that of the first sealing member 20A and three frame films 26B each formed of a film in addition to the first film 22B.

Referring to FIG. 14, each of the frame films 26B has a closed path shape. More specifically, each of the frame films 26B is a thin sheet having a rectangular frame shape and is bendable. Each of the frame films 26B has an outer edge which has a rectangular shape in the XY-plane. Each of the frame films 26B is formed with a center hole 266B. Each of the center holes 266B has a rectangular shape in the XY-plane and passes through the frame film 26B in the Z-direction. Each of the frame films 26B of the present modification has the aforementioned structure. However, the structure of each of the frame films 26B is not specifically limited, provided that each of the frame films 26B has a closed, or seamless, frame shape. For example, each of the frame films 26B may have a circular frame shape.

Each of the frame films 26B has a film-seal portion 262B and a circuit-seal portion 264B. The circuit-seal portion 264B of the present modification is a part of the frame film 26B which is located around the center hole 266B and has a rectangular frame shape. The circuit-seal portion 264B surrounds the center hole 266B throughout its entire circumference in the XY-plane. The film-seal portion 262B of the present modification is another part of the frame film 26B which is located around the circuit-seal portion 264B and has a rectangular frame shape. The film-seal portion 262B surrounds the circuit-seal portion 264B throughout its entire circumference in the XY-plane. In the present modification, there is no visible boundary between the film-seal portion 262B and the circuit-seal portion 264B. However, the present invention is not limited thereto. For example, a visible boundary may be formed between the film-seal portion 262B and the circuit-seal portion 264B.

Each of the frame films 26B of the present modification is formed of an ultraviolet-curing tape. More specifically, each of the frame films 26B contains a pressure-sensitive adhesive which can be adhered to another member when pressed against the member and an ultraviolet-curing resin which can be hardened when exposed to ultraviolet light. Thus, each of the film-seal portions 262B and the circuit-seal portions 264B contains a pressure-sensitive adhesive and an ultraviolet-curing resin. For example, when the film-seal portion 262B is pressed against another member, the frame film 26B is adhered to this member. Thereafter, when ultraviolet light is radiated to the frame film 26B, the frame film 26B is hardened and is bonded to this member.

Each of the frame films 26B of the present modification has a lower layer and an upper layer. The lower layer is made of resin which contains a pressure-sensitive adhesive and an ultraviolet-curing resin. The upper layer is made of resin which contains no pressure-sensitive adhesive and no ultraviolet-curing resin. Thus, each of the film-seal portions 262B and the circuit-seal portions 264B has a lower surface which can be adhered and bonded to another member. In contrast, each of the film-seal portions 262B and the circuit-seal portions 264B has an upper surface which cannot be adhered to another member merely by pressing against another member. However, the present invention is not limited thereto. For example, the resin of the upper layer of the frame film 26B may contain a pressure-sensitive adhesive and an ultraviolet-curing resin similar to those of the lower layer.

The three frame films 26B are provided so as to correspond to the three openings 244B of the first film 22B, respectively. The number of the frame films 26B is not limited to three but should be equal to the number of the openings 244B. Each of the openings 244B has a size in the XY-plane which is smaller than a size of the corresponding frame film 26B in the XY-plane but is larger than a size of the center hole 266B of the corresponding frame film 26B in the XY-plane.

Referring to FIG. 13 together with FIG. 14, each of the frame films 26B is arranged on the outer surface 232A of the first film 22B so that the corresponding opening 244B is located inward of the outer edge of the frame film 26B and is located outward of the center hole 266B in the XY-plane. In other words, each of the frame films 26B is arranged on the outer surface 232A so as to cover the edge portion 245B of the corresponding opening 244B throughout its entire circumference. The film-seal portion 262B of each of the frame films 26B which are arranged as described above is adhered to the outer surface 232A. The film-seal portion 262B is located around the opening 244B in the XY-plane and seals off the edge portion 245B of the opening 244B throughout its entire circumference.

The film-seal portions 262B of the present modification can be bonded to the outer surface 232A by radiating ultraviolet light after they are adhered to the outer surface 232A. Thus, each of the frame films 26B can be bonded to the outer surface 232A of the first film 22B by using the pressure-sensitive adhesive and the ultraviolet-curing resin contained in the film-seal portion 262B. However, the present invention is not limited thereto. For example, the frame film 26B may be bonded to the outer surface 232A of the first film 22B by using a fixing member such as an adhesive other than the frame film 26B. When the frame film 26B can be bonded to another member only by using a pressure-sensitive adhesive, the frame film 26B does not need to contain an ultraviolet-curing resin. Thus, the frame film 26B may be a simple adhesive tape.

The frame film 26B may be bonded to the inner surface 234A (see FIG. 15) of the first film 22B after it is adhered thereon. In this instance, the opening 244B may be located inward of the center hole 266B in the XY-plane. Moreover, the upper layer of the frame film 26B may be provided with a meltable layer and may be fused to the first film 22B.

According to the present modification, when each of the film-seal portions 262B is adhered on the outer surface 232A, the circuit-seal portion 264B is located inward of the opening 244B in the XY-plane. In other words, a part of each of the frame films 26B which is adhered on the outer surface 232A is the film-seal portion 262B, and another part of each of the frame films 26B which is located inward of the opening 244B in the XY-plane so as not to be adhered on the outer surface 232A is the circuit-seal portion 264B. However, the present invention is not limited thereto. For example, when the frame film 26B is adhered on the inner surface 234A (see FIG. 15) of the first film 22B, a part of the upper surface of the frame film 26B which is adhered on the inner surface 234A is the film-seal portion 262B, and the lower surface of the frame film 26B is the circuit-seal portion 264B.

Referring to FIG. 5, each of the first bodies 41 of the first circuit member 40 has an exposed portion 424 and a seal portion 426. Each of the exposed portion 424 and the seal portion 426 is a part of an upper surface of the first body 41. The exposed portion 424 of each of the first bodies 41 surrounds the main electrode 422 throughout its entire circumference in the XY-plane. In other words, the main electrodes 422 are provided on the exposed portions 424, respectively. The seal portion 426 of each of the first bodies 41 surrounds the exposed portion 424 throughout its entire circumference in the XY-plane.

In the present modification, there is no visible boundary between the exposed portion 424 and the seal portion 426. Moreover, there is no visible boundary at a circumference of the seal portion 426 in the XY-plane. However, the present invention is not limited thereto. For example, a visible boundary may be formed between the exposed portion 424 and the seal portion 426.

Referring to FIG. 5 together with FIG. 4, the exposed portion 424 and the seal portion 426 of the present modification are provided on each of the first bodies 41. However, the present invention is not limited thereto. For example, when the main electrode 422 is provided on the second body 51 of the second circuit member 50, the exposed portion 424 and the seal portion 426 are parts of the upper surface of the second body 51. Thus, at least one of the first bodies 41, the second body 51 and the third bodies 61 may comprise the exposed portion 424 and the seal portion 426. In any instance, the number of the exposed portions 424 may be equal to the number of the main electrodes 422, and the number of the seal portions 426 may be equal to the number of the exposed portions 424.

Figure 15:
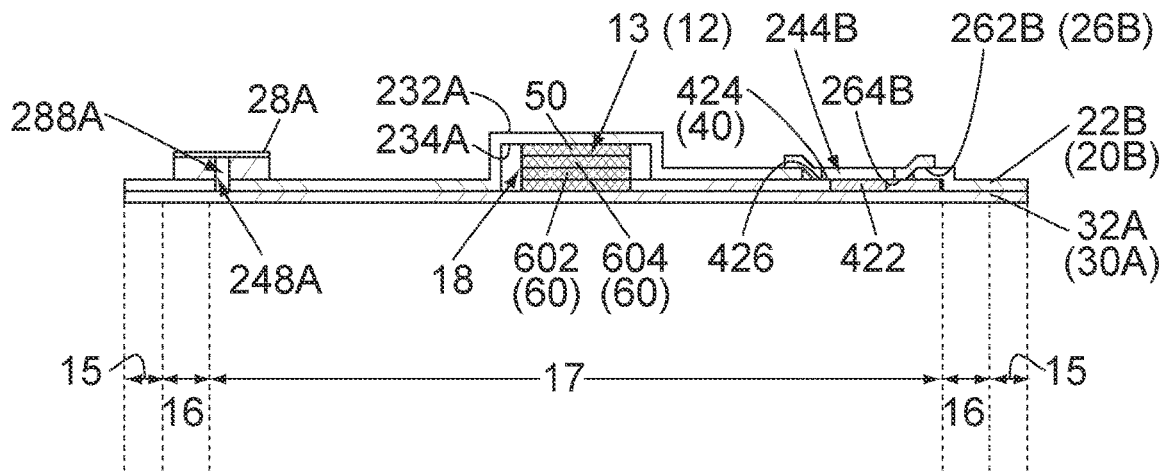
FIG. 15 is a schematic, edge view showing the device of FIG. 13, taken along line XV-XV, wherein the inner structure of the device is merely schematically illustrated, the size and arrangement of each member are not equal to the actual size and arrangement thereof.

Referring to FIG. 15, the device 10B can be formed by a forming method similar to that of the device 10A (see FIG. 12). However, the frame films 26B have been adhered to the first film 22B and the seal portions 426 when the vacuuming step starts. In detail, the film-seal portion 262B of each of the frame films 26B is bonded to the first film 22B so as to surround the opening 244B throughout its entire circumference. The circuit-seal portion 264B of each of the frame films 26B is bonded to the seal portion 426 so as to surround the exposed portion 424 throughout its entire circumference. As a result, air passages through the openings 244B are blocked.

The film-seal portions 262B and the circuit-seal portions 264B of the present modification are bonded by using the pressure-sensitive adhesive and the ultraviolet-curing resin. However, the present invention is not limited thereto. For example, the circuit-seal portions 264B may be bonded to the seal portions 426, respectively, by using a fixing member such as an adhesive other than the frame films 26B. Moreover, the shape of each of the exposed portions 424 and the seal portions 426 is not specifically limited, provided that the frame films 26B can be bonded to the first film 22B and the seal portions 426 so as to block the air passages.

As a result of the vacuuming step, the device 10B is formed with the closed space 18 similar to that of the device 10A (see FIG. 12). The closed space 18 is enclosed by the first sealing member 20B and the second sealing member 30A except for the exposed portions 424 and is shut off from an outer space outside the device 10B. Air pressure of the closed space 18 is kept to low pressure lower than the atmospheric pressure.

The device 10B which is formed as described above works similarly to the device 10A (see FIG. 12). For example, a contact force is generated because of air pressure difference between the inside and the outside of the closed space 18, and thereby the contact between the first electrodes 462 (see FIG. 3), the second electrodes 562 (see FIG. 3) and the third electrodes 662 (see FIG. 3) can be securely kept without using a fixing member such as an adhesive since.

Referring to FIGS. 13 and 15, the exposed portions 424 and the seal portions 426 of the fabricated device 10B face the first film 22B in the upper-lower direction. Each of the seal portions 426 is located just under the circuit-seal portion 264B of the frame film 26B. Each of the exposed portions 424 is located at the middle of opening 244B in the XY-pane and is exposed upward through the center hole 266B of the frame film 26B. In other words, parts of the first circuit member 40 (see FIG. 4) which are exposed through the center holes 266B are the exposed portions 424.

As described above, the exposed portions 424 are exposed to the outer space located outside the device 10B. Each of the first circuit member 40, the second circuit member 50 and the third circuit members 60 is shut in the closed space 18 maintained to the aforementioned low pressure except for the exposed portions 424. In other words, no part of the circuit structure 12 is located outside the device 10B except for the exposed portions 424.

The device 10B can be used similarly to the device 10A (see FIG. 12). For example, biological signals can be accurately obtained via the main electrodes 422 which are located on the exposed portions 424 and are in contact with a skin of a subject. The main electrodes 422 may be in direct contact with the skin of the subject or may be in indirect contact with the skin of the subject via a soft conductive member such as a conductive gel. Thus, the device 10B may further comprise conductive gels which cover the frame films 26B.

Figure 16:
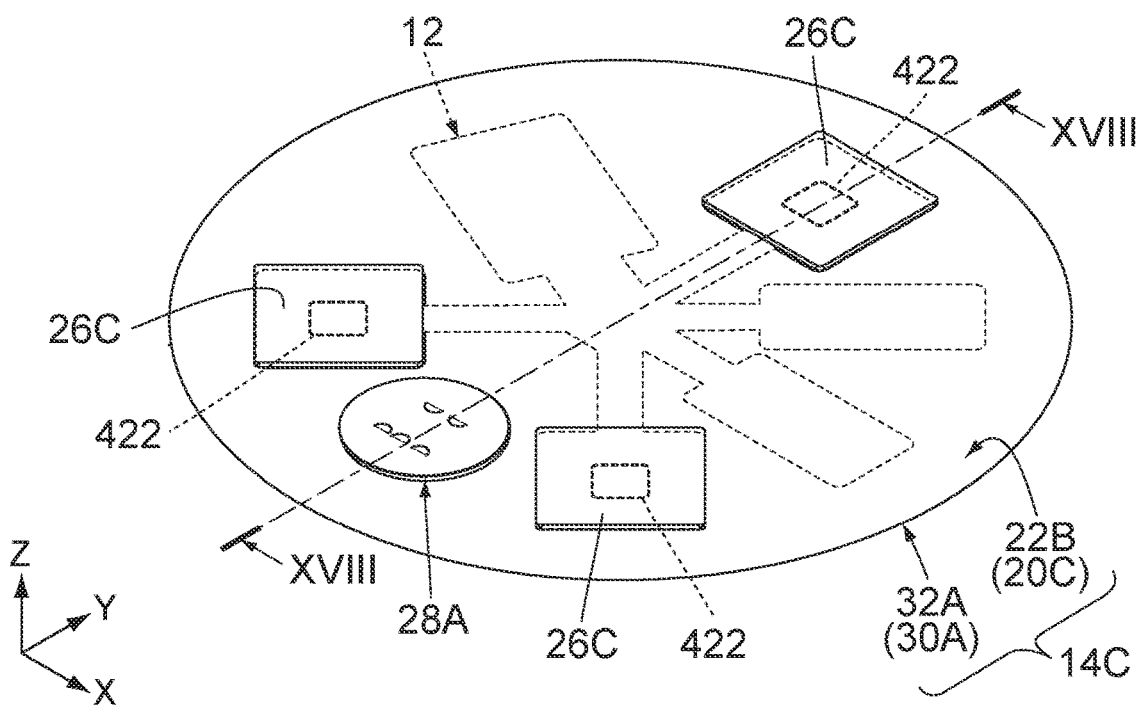
FIG. 16 is a perspective view showing a third modification of the device of FIG. 1, wherein an outline of the hidden circuit structure is illustrated with dashed line.

Comparing FIG. 16 with FIG. 13, a device 10C according to a third modification comprises the circuit structure 12 and the second sealing member 30A same as those of the device 10B. In addition, the device 10C comprises a first sealing member 20C different from the first sealing member 20B of the device 10B. Thus, the device 10C comprises a sealing member 14C consisting of the first sealing member 20C and the second sealing member 30A.

Figure 17:
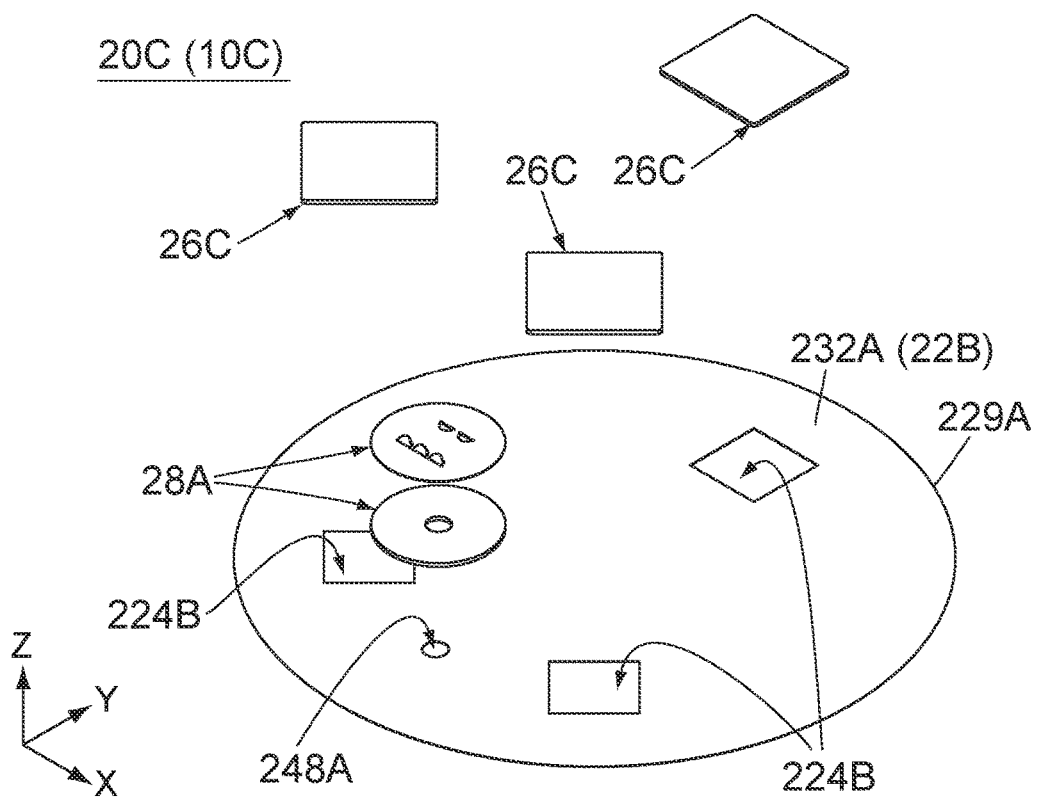
FIG. 17 is an exploded, perspective view showing a first sealing member of the device of FIG. 16, wherein the valves of the air valve are open.

Comparing FIG. 17 with FIG. 14, the first sealing member 20C comprises, as a base of the first sealing member 20C, the first film 22B formed of a film and comprises the air valve 28A similarly to the first sealing member 20B. However, the first sealing member 20C comprises three conductive gels 26C instead of the frame films 26B. The conductive gels 26C are provided so as to correspond to the three openings 244B of the first film 22B, respectively.

Figure 18:
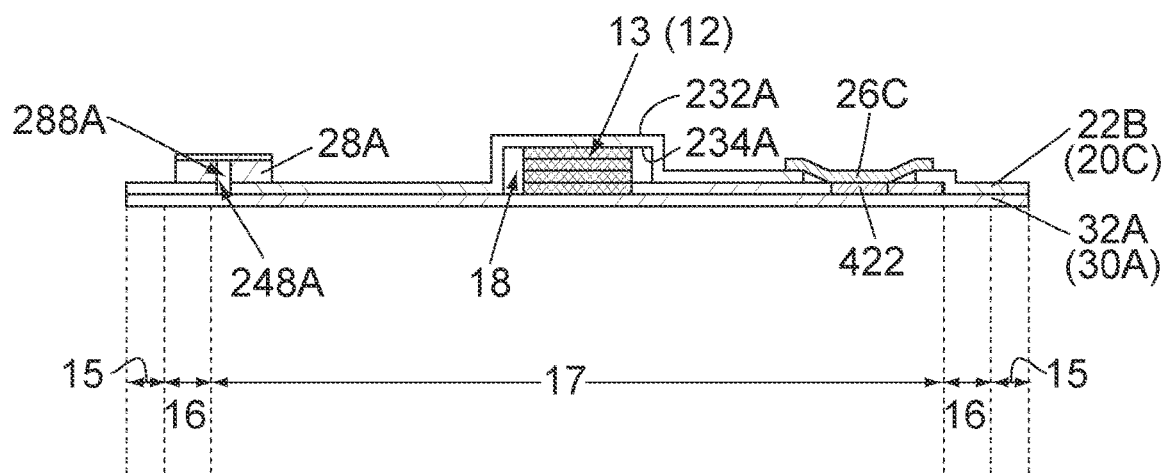
FIG. 18 is a schematic, edge view showing the device of FIG. 16, taken along line XVIII-XVIII, wherein the inner structure of the device is merely schematically illustrated, the size and arrangement of each member are not equal to the actual size and arrangement thereof.
Figure 19:
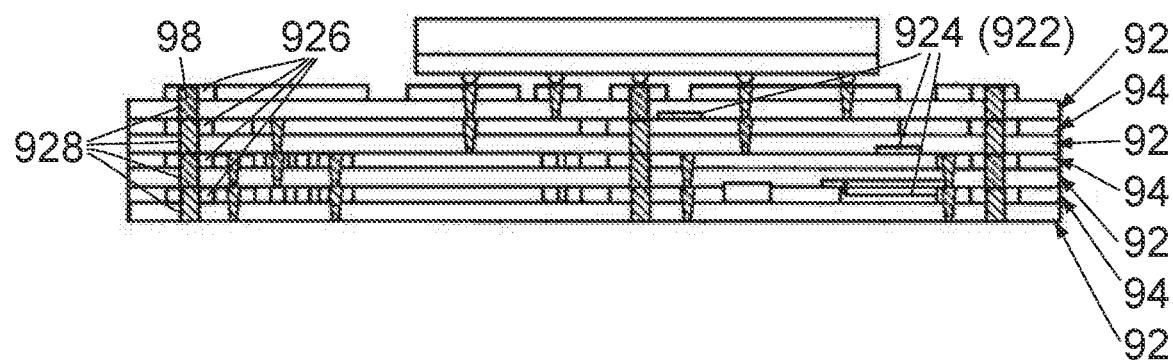
FIG. 19 is a cross-sectional view showing a device of Patent Document 1.

Referring to FIGS. 16 and 18 together with FIGS. 13 and 15, the device 10C is formed by a forming method similar to that of the device 10B. However, the conductive gels 26C are glued and fixed to the first film 22B without using a fixing member such as an adhesive tape (not shown). In detail, each of the conductive gels 26C is bonded to the first film 22B so as to wholly cover the corresponding opening 244B. Referring to FIG. 18, each of the conductive gels 26C of the present modification is bonded to the outer surface 232A of the first film 22B. However, the present invention is not limited thereto. For example, each of the conductive gels 26C may be bonded to the inner surface 234A of the first film 22B.

Except for the differences described above, the device 10C has a structure similar to that of the device 10B and works similarly to the device 10B. For example, the conductive gels 26C are in contact with the main electrodes 422 in the device, respectively, and are partially exposed to the outer space located outside the device 10C. Biological signals can be accurately obtained via the soft conductive gels 26C which are in contact with a skin of a subject. A contact force is generated because of air pressure difference between the inside and the outside of the closed space 18, and thereby the contact between the conductive gels 26C and the main electrodes 422 can be securely kept without using a fixing member such as an adhesive. Moreover, the contact between the first electrodes 462 (see FIG. 3), the second electrodes 562 (see FIG. 3) and the third electrodes 662 (see FIG. 3) can be securely kept without using a fixing member such as an adhesive because of a similar contact force.

Referring to FIGS. 12, 15 and 18, according to the first to third modifications, the closed space 18 is, at least in part, enclosed by the first sealing member and the second sealing member. Each of the first circuit member, the second circuit member and the third circuit members is, at least in part, shut in the closed space 18.

The first to third modifications can be further variously modified. For example, referring to FIG. 9, the peripheral edge 229A of the first film 22A and the peripheral edge 329A of the second film 32A may be partially connected to each other. In other words, each of the first film 22A and the second film 32A may be a part of a single planar sheet.

Referring to FIGS. 1, 9, 13 and 16, the device of the embodiment and the modifications described above has a shape which does not hurt a skin of a subject. For example, the corners of the circuit structure 12 are chamfered in arc shapes. The sheet-like member such as the sealing members 14A, 14B and 14C has a circular shape.

However, the present invention is not limited thereto. For example, the sheet-like member may have a rectangular shape in the XY-plane. In this instance, the air valve 28A may be located in the vicinity of a predetermined side of the sheet-like member. Moreover, an openable and closable fastener may be provided between the predetermined side and the air valve 28A. In this instance, vacuuming may be performed under a state where the fastener is closed. Thereafter, the first film 22A and the second film 32A may be fused to each other at a predetermined position located between the air valve 28A and the circuit structure 12. The part provided with the air valve 28A may be cut off after the fusing. Thus, each of the devices 10A, 10B and 10C may comprise no air valve 28A.

What is claimed is:

1. A device comprising a first circuit member, a second circuit member and at least one third circuit member, wherein:
   the first circuit member comprises a first body and a first flexible board and is formed with a first wiring;
   the first body and the first flexible board are coupled to each other;
   the first body has a first main portion configured to perform a function of the first circuit member;
   the first flexible board has a first integrated-electrode portion;
   the first integrated-electrode portion comprises a first insulation layer and is formed with two or more first electrodes held by the first insulation layer;
   the first wiring connects the first main portion to at least one of the first electrodes;
   the second circuit member comprises a second body and a second flexible board and is formed with a second wiring;
   the second body and the second flexible board are coupled to each other;
   the second body has a second main portion configured to perform a function of the second circuit member;
   the second flexible board has a second integrated-electrode portion;
   the second integrated-electrode portion comprises a second insulation layer and is formed with two or more second electrodes held by the second insulation layer;
   the second wiring connects the second main portion to at least one of the second electrodes;
   the third circuit member comprises a third body and a third flexible board and is formed with a third wiring;
   the third body and the third flexible board are coupled to each other;
   the third body has a third main portion configured to perform a function of the third circuit member;
   the third flexible board has a third integrated-electrode portion;
   the third integrated-electrode portion comprises a third insulation layer and is formed with two or more third electrodes held by the third insulation layer;
   the third wiring connects the third main portion to at least one of the third electrodes;
   the first integrated-electrode portion, the second integrated-electrode portion and the third integrated-electrode portion lie over each other in an upper-lower direction;
   the third integrated-electrode portion is located between the first integrated-electrode portion and the second integrated-electrode portion in the upper-lower direction;
   each of the first electrodes projects upward beyond an upper surface of the first integrated-electrode portion and is exposed upward;
   each of the second electrodes projects downward beyond a lower surface of the second integrated-electrode portion and is exposed downward;
   each of the third electrodes projects downward beyond a lower surface of the third integrated-electrode portion and projects upward beyond an upper surface of the third integrated-electrode portion;
   each of the third electrodes has an upper end surface exposed upward and a lower end surface exposed downward, the upper end surface and the lower end surface being electrically connected with each other;
   at least one of the first electrodes and at least one of the second electrodes are connected to each other via a predetermined one of the third electrodes; and
   the first body, second body and the third body are apart from each other when seen along the upper-lower direction.

2. The device as recited in claim 1, wherein:
   the first integrated-electrode portion is formed with a first predetermined number of the first electrodes;
   the second integrated-electrode portion is formed with a second predetermined number of the second electrodes;
   the third integrated-electrode portion is formed with a third predetermined number of the third electrodes;
   the first predetermined number, the second predetermined number and the third predetermined number are equal to each other;
   the first electrodes are arranged in a predetermined electrode arrangement, the second electrodes are arranged in the predetermined electrode arrangement, and the third electrodes are arranged in the predetermined electrode arrangement; and
   the first electrodes are connected to the second electrodes, respectively, via the third electrodes, respectively.

3. The device as recited in claim 1, wherein:
   the device comprises a first sealing member and a second sealing member;
   the device is formed with a closed space;
   the closed space is, at least in part, enclosed by the first sealing member and the second sealing member and is shut off from an outer space located outside the device;
   each of the first circuit member, the second circuit member and the third circuit member is, at least in part, shut in the closed space; and
   at least one of the first electrodes and at least one of the second electrodes are pressed against a predetermined one of the third electrodes to be connected to each other.

4. The device as recited in claim 3, wherein:
   the first sealing member comprises, as a base of the first sealing member, a first film formed of a film and comprises a conductive portion made of conductor;
   the closed space is enclosed by the first sealing member and the second sealing member;
   each of the first circuit member, the second circuit member and the third circuit member is shut in the closed space;
   at least one of the first main portion, the second main portion and the third main portion includes a main electrode; and
   the conductive portion is in contact with the main electrode in the closed space and is partially exposed to the outer space located outside the device.

5. The device as recited in claim 3, wherein:
   the first sealing member comprises, as a base of the first sealing member, a first film formed of a film and comprises a frame film formed of a film;
   the first film is formed with an opening;
   the opening is surrounded by an edge portion which forms a closed path;
   the frame film has a closed path shape;

at least one of the first main portion, the second main portion and the third main portion includes a main electrode;
at least one of the first body, the second body and the third body comprises an exposed portion and a seal portion;
the main electrode is provided on the exposed portion;
the exposed portion and the seal portion face the first film;
the seal portion surrounds the exposed portion throughout its entire circumference;
the frame film has a film-seal portion and a circuit-seal portion;
the film-seal portion is bonded to the first film so as to surround the opening throughout its entire circumference;
the circuit-seal portion is bonded to the seal portion so as to surround the exposed portion throughout its entire circumference;
the closed space is enclosed by the first sealing member and the second sealing member except for the exposed portion;
the exposed portion is exposed to the outer space located outside the device; and
each of the first circuit member, the second circuit member and the third circuit member is shut in the closed space except for the exposed portion.

6. The device as recited in claim 3, wherein:
the first sealing member comprises, as a base of the first sealing member, a first film formed of a film and comprises a conductive gel;
at least one of the first main portion, the second main portion and the third main portion includes a main electrode; and
the conductive gel is in contact with the main electrode in the device and is partially exposed to the outer space located outside the device.

7. The device as recited in claim 2, wherein:
the device comprises a first sealing member and a second sealing member;
the device is formed with a closed space;
the closed space is, at least in part, enclosed by the first sealing member and the second sealing member and is shut off from an outer space located outside the device;
each of the first circuit member, the second circuit member and the third circuit member is, at least in part, shut in the closed space; and
at least one of the first electrodes and at least one of the second electrodes are pressed against a predetermined one of the third electrodes to be connected to each other.

* * * * *